(12) United States Patent
Huang et al.

(10) Patent No.: US 11,400,083 B2
(45) Date of Patent: Aug. 2, 2022

(54) CXCR4 ANTAGONISTS WITH AMINO ACID SKELETON, PREPARATION THEREFOR AND BIOMEDICAL USE THEREOF

(71) Applicant: Tsinghua University, Beijing (CN)

(72) Inventors: Ziwei Huang, Beijing (CN); Xiong Fang, Beijing (CN); Qian Meng, Beijing (CN); Yan Xu, Beijing (CN); Siyu Zhu, Beijing (CN); Xiao Fang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 9 days.

(21) Appl. No.: 16/650,924

(22) PCT Filed: Dec. 1, 2017

(86) PCT No.: PCT/CN2017/114318
§ 371 (c)(1),
(2) Date: Mar. 26, 2020

(87) PCT Pub. No.: WO2019/061812
PCT Pub. Date: Apr. 4, 2019

(65) Prior Publication Data
US 2020/0268729 A1   Aug. 27, 2020

(30) Foreign Application Priority Data
Sep. 28, 2017   (CN) .......................... 201710901067.6

(51) Int. Cl.
| | | |
|---|---|---|
| *C07D 213/56* | (2006.01) |
| *A61K 31/4439* | (2006.01) |
| *A61K 31/165* | (2006.01) |
| *A61K 31/417* | (2006.01) |
| *A61K 31/4402* | (2006.01) |
| *A61K 31/47* | (2006.01) |
| *A61K 45/06* | (2006.01) |
| *C07D 215/40* | (2006.01) |
| *C07D 233/64* | (2006.01) |
| *C07D 401/06* | (2006.01) |
| *C07D 401/12* | (2006.01) |

(52) U.S. Cl.
CPC ........ *A61K 31/4439* (2013.01); *A61K 31/165* (2013.01); *A61K 31/417* (2013.01); *A61K 31/4402* (2013.01); *A61K 31/47* (2013.01); *A61K 45/06* (2013.01); *C07D 213/56* (2013.01); *C07D 215/40* (2013.01); *C07D 233/64* (2013.01); *C07D 401/06* (2013.01); *C07D 401/12* (2013.01)

(58) Field of Classification Search
None
See application file for complete search history.

(56) References Cited

PUBLICATIONS

WIPO, ISR for PCT/CN2017/114318, dated Jun. 21, 2018.
SIPO, Second Office Action for CN Application No. 201710901067.6, dated May 14, 2020.
Chemical Abstracts Service, retrieved from the internet Aug. 2020: <https://www.chemeurope.com/en/encyclopedia/Chemical_Abstracts_Service.html>.

*Primary Examiner* — Samantha L Shterengarts
(74) *Attorney, Agent, or Firm* — Hodgson Russ LLP

(57) ABSTRACT

The present invention provides a compound represented by formula (I), or a pharmaceutically acceptable salt or prodrug thereof.

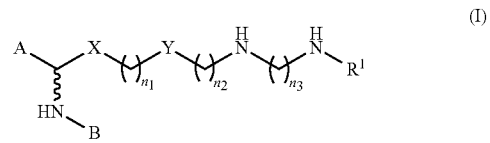

(I)

12 Claims, 2 Drawing Sheets

CXCR4 ANTAGONISTS WITH AMINO ACID SKELETON, PREPARATION THEREFOR AND BIOMEDICAL USE THEREOF

CROSS-REFERENCE TO RELATED APPLICATION

This application is a U.S. national phase of International Application No. PCT/CN2017/114318, filed Dec. 1, 2017, which claims priority to Chinese Patent Application No. 201710901067.6, filed Sep. 28, 2017, the entire disclosures of which are incorporated herein by reference.

TECHNICAL FIELD

The present disclosure relates to the field of pharmaceutical chemistry, and more particularly to novel CXCR4 antagonists with amino acid skeleton and to the preparation and biomedical application thereof.

BACKGROUND

Chemokine receptors are a superfamily of G protein-coupled receptors (GPCRs) having seven transmembrane structures, which are usually expressed on cell membranes of various types of cells including immune cells, epithelial cells, vascular endothelial cells and nerve cells. CXCR4, one of CXC chemokine receptors, and its natural ligand chemokine CXCL12 (stromal cell-derived factor-1, SDF-1) are widely expressed in a variety of cells and tissues, they play an important role in regulating the immune system, circulatory system and nervous system of the human body. CXCR4 and CXCR12/SDF-1 interaction and the signal transduction mediated by them are closely related to various diseases, such as viral infection, tumor progress and metastasis, inflammation and autoimmune diseases.

Early studies have shown that HIV-1 can successfully invade and infect human body involving in a major receptor CD4 and two chemokine receptors (CXCR4 and CCR5). CXCR4 together with CCR5 act as important co-receptors of HIV-1 infection. Based on the difference of the co-receptors, the HIV virus may be classified into three categories: (1) macrophage virus mainly utilizing CCR5 receptor, namely R5 virus strain; (2) T-cell phagocytic virus mainly utilizing CXCR4 receptor, namely X4 virus strain; (3) dual phagocytic virus utilizing both CCR5 and CXCR4, namely R5X4 virus strain. Co-receptors have become one of the important targets for anti-HIV, and the development of new anti-HIV agent towards CXCR4 or CCR5 antagonist has been widely concerned. At present, maraviroc is the only one CCR5 antagonist approved by FDA in 2007, which is used in combination with other antiretroviral agents to treat R5-type HIV-1 infected adults who have previously received therapy, there is no CXCR4 antagonist against HIV on the market. Moreover, the clinical use of maraviroc requires virus detection and it cannot be used to treat HIV-1 infections caused by X4 and R5X4 virus strains. Therefore, although developing novel CXCR4 antagonists for the treatment of HIV faces great challenges, there are great prospects. This may not only overcome the shortcomings of the current single co-receptor inhibitor, but also provide more combinations of agents for the treatment of HIV.

Recent studies have found that CXCR4 is highly expressed on many solid tumors including breast cancer, lung cancer, prostate cancer, colon cancer, ovarian cancer, pancreatic cancer, and glioma. CXCL12-CXCR4 axis mediates the proliferation of tumor cells and the neovascularization by regulating its downstream signal pathway, which plays important roles in tumor microenvironment and tumor cell invasion and metastasis. In addition, CXCR4 is widely expressed on hematopoietic cells, and CXCL12-CXCR4 interaction regulates the homing of hematopoietic stem cells to the bone marrow. In malignant hematological diseases, CXCR4-overexpressing leukemia cells and multiple myelomacells can migrate to the bone marrow stroma by the CXCL12-CXCR4 axis, thereby obtaining the ability for survival, proliferation and drug resistance. Meanwhile, the migration mediated by the CXCL12-CXCR4 axis will also cause the infiltration of leukemia cells into extramedullary tissues, such as liver, spleen, lung, brain and lymphoid tissues that highly express CXCL12. Therefore, the combined utilization of CXCR4 antagonists and chemotherapeutic agents has become a new hotspot in the research of anti-tumor proliferation and metastasis. Using the CXCR4 antagonists to interfere with or block CXCL12-CXCR4 interaction not only provide new therapeutics for anti-tumor metastasis, but also destroy the protection of bone marrow microenvironment, inhibit the migration and infiltration of leukemia cells into and out of the bone marrow, mobilize leukemia cells into the peripheral blood, so as to improve the sensitivity of leukemia cells to the chemotherapeutics.

At present, only one CXCR4 antagonist, plerixafor (AMD3100), has been approved by FDA as a hematopoietic stem cell mobilizer in combination with granulocyte colony stimulating factor (G-CSF) for the treatment of patients with multiple myeloma and non-hodgkin lymphoma who receive the bone-marrow stem cell transplantation. However, this is far from meeting the clinical needs.

In conclusion, it is extremely challenging and promising that the design and development of CXCR4 antagonists with novel and diverse structures bearing high efficiency and low toxicity may provide more potential lead molecules and candidates for mobilizing stem cells and treating acute or chronic leukemia, multiple myeloma, and HIV.

SUMMARY

The present application is based on the inventors' discoveries and recognitions below.

Maraviroc is the only one CCR5 antagonist approved by FDA in combination with other antiretroviral agents to treat R5-type HIV-1 infected adults who have previously received therapy, there is no CXCR4 antagonist against HIV on the market. Moreover, there is only one CXCR4 antagonist, plerixafor (AMD3100), has been approved by FDA as a hematopoietic stem cell mobilizer in combination with granulocyte colony stimulating factor (G-CSF) for the treatment of patients with multiple myeloma and non-hodgkin lymphoma. Thus, the clinical needs are far from being met.

Based on the above recognitions, the inventors developed a new class of compounds with amino acid skeletons featuring novelty, efficiency, and low-toxicity. These compounds have excellent CXCR4 antagonistic activity, which are able to block HIV from invading and infecting human target cells, or treat or prevent AIDS, or mobilize human bone marrow hematopoietic cells, mesenchymal stem cells and stem cells, or interfere with cell migration and adhesion mediated by CXCL12/CXCR4, or prevent or treat tumor metastasis, invasion and growth mediated by CXCR4, or block autoimmune and inflammatory responses mediated by CXCL12/CXCR4. Moreover, such compounds may be used as an active ingredient of a pharmaceutical composition for preventing or treating HIV in combination with other anti-HIV agents, or preventing or treating tumors in combination with other agents used for the treatment or prevention of leukemia, lymphoma, myeloma and solid tumor. Furthermore, the inventors also provide design approaches, synthesis schemes, and preparation methods of such compounds.

In a first aspect, the present disclosure provides a compound of formula (I), or a pharmaceutically acceptable salt or prodrug thereof:

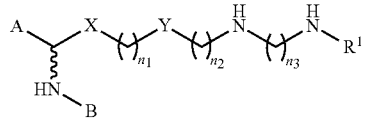

(I)

wherein $n_1$, $n_2$ and $n_3$ are each independently an integer of 0 to 3;

$R^1$ represents hydrogen, methyl, a linear or branched alkyl having two or more carbon atoms, a 5-7 membered cycloalkyl or optionally substituted cycloalkyl;

X represents —C(=O)NR²—, —CH₂C(=O)NR²—, —CH₂CH₂C(=O)NR²—, —CH₂NR²— and —CH₂CH₂NR²—, wherein $R^2$ represents hydrogen, methyl, or a linear or branched alkyl having two or more carbon atoms;

Y represents an optionally substituted 6-15 membered aromatic ring, an optionally substituted 5-15 membered heteroaromatic ring, or an optionally substituted 3-15 membered saturated carbocyclic ring;

A represents hydrogen, methyl, a linear or branched alkyl having two or more carbon atoms, a linear or branched alkyl substituted with a nitrogen, oxygen or sulfur atom, an optionally substituted 5-15 membered aryl or heteroaryl, an optionally substituted 3-15 membered saturated carbocyclic or heterocyclic alkyl, or a group of formula (i) or (ii):

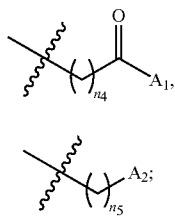

(i)

(ii)

wherein $n_4$ is an integer of 1 to 4, $A_1$ represents hydrogen, hydroxyl, sulfydryl, amino, alkoxy, alkylthio, aryl alkoxy, heteroaryl alkoxy, saturated cyclic hydrocarbyl alkoxy, alkyl substituted amino, aryl substituted amino, or heteroaryl substituted amino;

$n_5$ is an integer of 1 to 4, $A_2$ represents an optionally substituted 5-20 membered aromatic ring, 5-20 membered heteroaromatic ring, 5-20 unsaturated or partially saturated heterocyclic ring, 5-20 partially saturated carbocyclic ring, 3-15 membered saturated carbocyclic ring, 3-15 membered saturated heterocyclic ring, or a group of formula (iii) or (iv):

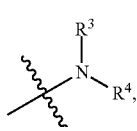

(iii)

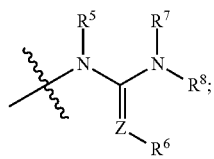

(iv)

wherein $R^3$, $R^4$, $R^5$, $R^6$, $R^7$, $R^8$ are each independently hydrogen, methyl, an optionally substituted alkyl, an optionally substituted carbonyl, an optionally substituted thiocarbonyl, an optionally substituted sulfonyl, an optionally substituted 5-15 membered aryl, an optionally substituted heteroaryl, an optionally substituted 3-15 membered saturated carbocyclic ring, or an optionally substituted heterocyclic ring;

Z represents a nitrogen, oxygen, or sulfur atom;

A can form a monocyclic or bicyclic ring together with HN⤳ ;

B represents hydrogen, alkyl, cycloalkyl, aryl, heteroaryl, an amino acid substituent, or a group of formula (v) or (vi):

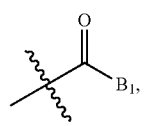

(v)

(vi)

wherein $B_1$, $B_2$ are each independently an optionally substituted cycloalkyl, aryl or heteroaryl.

It should be noted that the wavy line in HN⤳ represents that a relative configuration of the amino acid is L-type or D-type, and an absolute configuration of the compound of formula (I) is R-type, S-type or racemate.

The compounds according to embodiments of the present disclosure have a novel structure, are highly efficient and low-toxic, have excellent CXCR4 antagonistic activity, and are able to block HIV from invading and infecting human target cells, or treat or prevent AIDS, or mobilize human bone marrow hematopoietic cells, mesenchymal stem cells and stem cells, or interfere with cell migration and adhesion mediated by CXCL12/CXCR4, or prevent or treat tumor metastasis, invasion and growth mediated by CXCR4, or block autoimmune and inflammatory responses mediated by CXCL12/CXCR4. Moreover, such compounds may be used as an active ingredient of a pharmaceutical composition for preventing or treating HIV in combination with other anti-HIV agents or for preventing or treating tumors in combination with other agents used for the treatment or prevention of leukemia, lymphoma, myeloma and solid tumor.

According to embodiments of the present disclosure, the compound further includes at least one of the following additional technical features.

In some embodiments of the present disclosure, B in the compound of formula (I) includes the following cases: (1) when B is the cycloalkyl, B is preferably cyclopentyl, cyclohexyl, mono- or poly-substituted cyclohexyl methyl, pyridine-fused cyclohexyl; (2) when B is the aryl, B is preferably phenyl, biphenyl, or naphthyl; (3) when B is the heteroaryl, B is preferably imidazolyl, unsubstituted pyridyl, mono- or poly-substituted pyridyl; (4) when B is the amino acid substituent, B is preferably an L- or D-α-amino acid; (5) when B is aryl-, heteroaryl-, saturated carbocyclic or heterocyclic ring-substituted alkyl or formyl, B is preferably

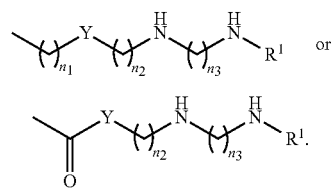

In some embodiments of the present disclosure, in the compound of formula (I), when $n_1$ and $n_2$ are each 1 or 2, $n_3$ is 3 or 4; when $n_1=0$, X and Y are connected directly; when $n_2=0$, Y is directly connected to the N atom; and when $n_3=0$, only one N atom is directly connected to $R^1$.

In some embodiments of the present disclosure, $R^1$ in the compound of formula (I) includes the following cases: (1) when $R^1$ is a $C_{1-3}$ alkyl, $R^1$ is preferably methyl, ethyl, propyl or isopropyl; (2) when $R^1$ is an optionally substituted saturated carbocyclic alkyl or an alkyl substituted with a saturated carbocyclic alkyl, the saturated carbocyclic alkyl is preferably cyclopropyl, cyclopentyl, or cyclohexyl.

In an embodiment of the present disclosure, Y in the compound of formula (I) is of a ring structure connected preferably at para-positions, and the ring structure is selected from a group including pyrrole, benzene, pyridine, cyclopropane, cyclobutane, cyclopentane, and cyclohexane.

In an embodiment of the present disclosure,

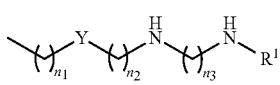

in the compound of formula (I) includes:

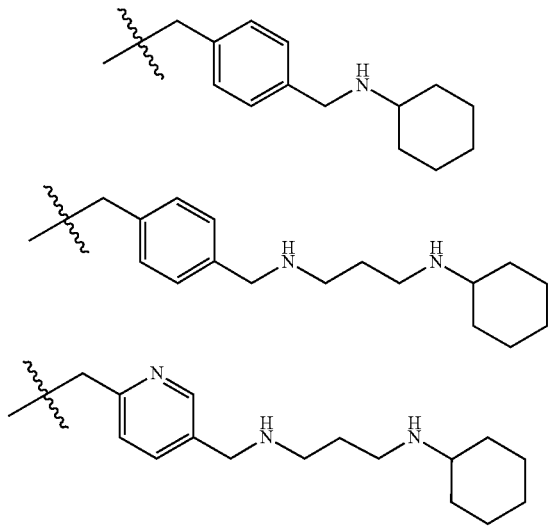

-continued

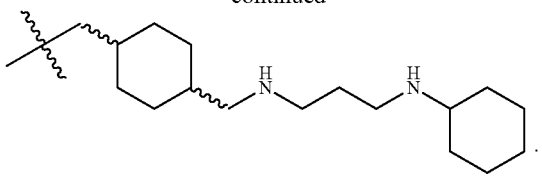

In an embodiment of the present disclosure,

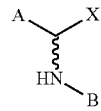

is an amino acid, and the amino acid is a natural or non-natural amino acid.

In an embodiment of the present disclosure, the amino acid includes an α-amino acid, a β-amino acid, or a γ-amino acid. The α-amino acid has a linear or cyclic structure depending on whether a side chain of the α-amino acid is cyclized with an —NH$_2$ terminal, and the amino acid includes an L- or D-amino acid.

In an embodiment of the present disclosure, the α-amino acid includes at least one selected from a group including arginine, lysine, citrulline, ornithine, histidine, aspartic acid, glutamic acid, glutamine, asparagine, serine, threonine, cysteine, phenylalanine, 3-(2-naphthyl) alanine, cyclohexylalanine, tryptophan, 5-hydroxytryptophan, tyrosine, glycine, phenylglycine, cyclohexylglycine, alanine, valine, leucine, isoleucine, methionine, proline, 4-hydroxyproline, 1-amino-1-cyclohexanecarboxylic acid and 1,2,3,4-tetrahydroisoquinolyl-3-carboxylic acid.

In an embodiment of the present disclosure, A in the compound of formula (I) is

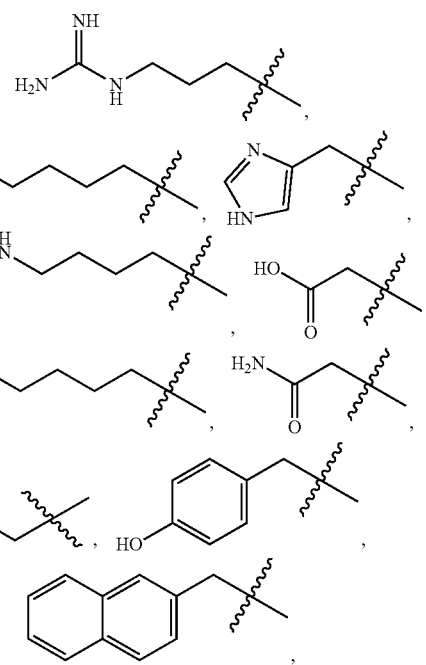

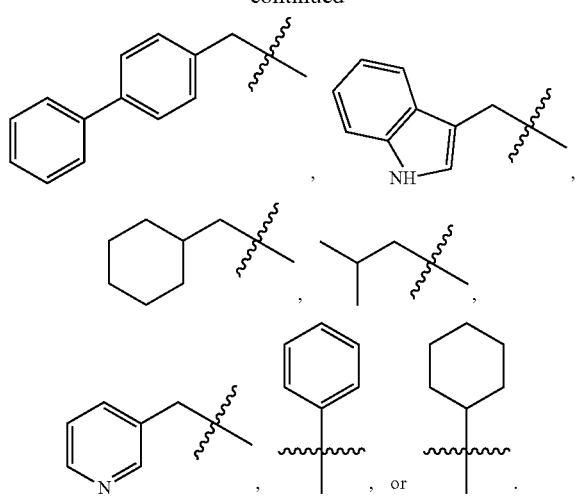

In an embodiment of the present disclosure, A in the compound of formula (I) forms a monocyclic ring together with HN~, and the compound of formula (I) has the following structures:

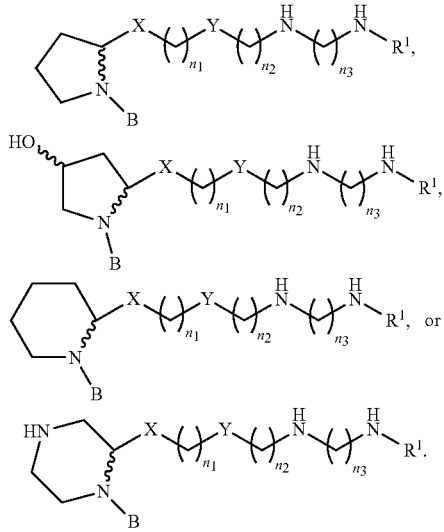

In an embodiment of the present disclosure, A in the compound of formula (I) forms a bicyclic ring together with HN~, and the compound of formula (I) has the following structures:

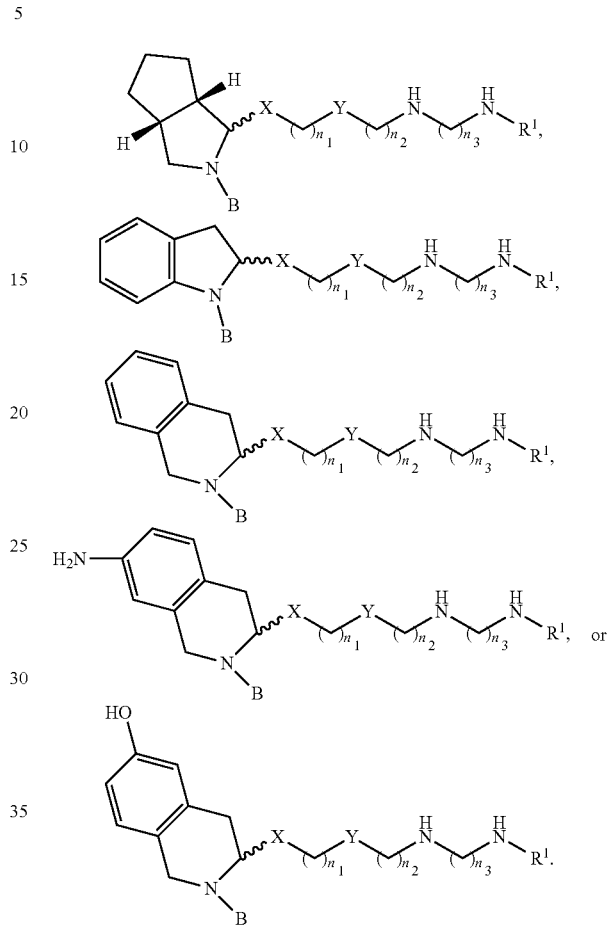

In an embodiment of the present disclosure, the pharmaceutically acceptable salt of the compound of formula (I) includes at least one selected from a group including trifluoroacetate, hydrochloride, acetate, sulfate, mesylate, tosylate, citrate, tartrate, fumarate, maleate and malate.

In a second aspect, the present disclosure provides a compound. In an embodiment of the present disclosure, the compound includes one of the following structures, or a pharmaceutically acceptable salt or prodrug thereof:

(1)

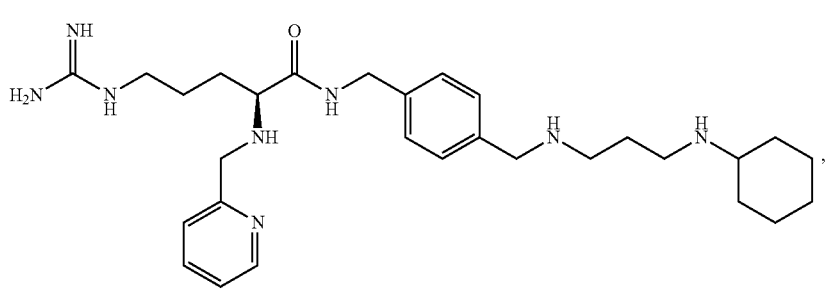

-continued
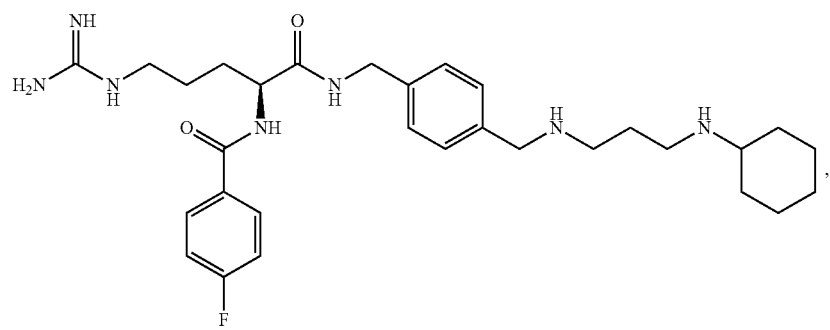
(2)
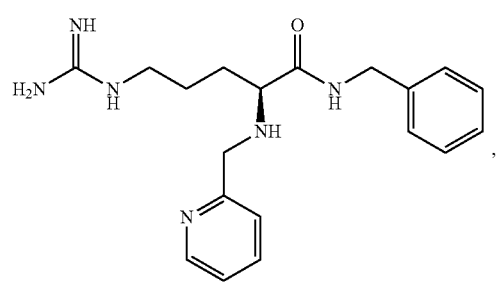
(3)
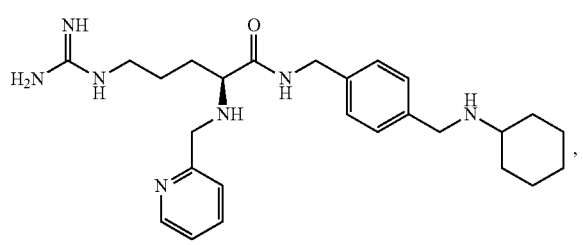
(4)
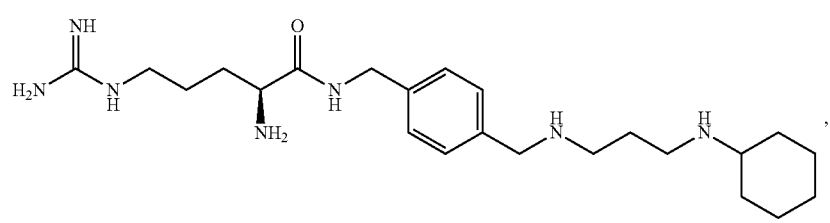
(5)
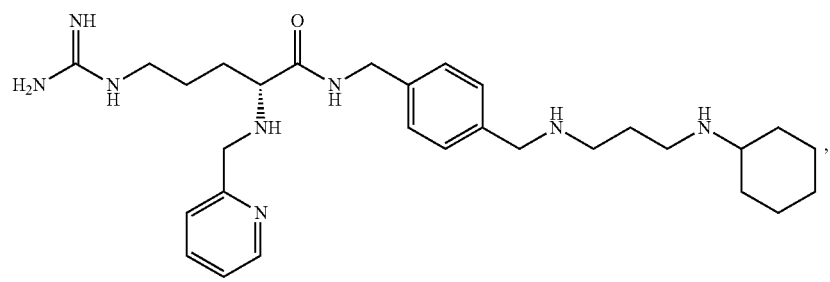
(6)
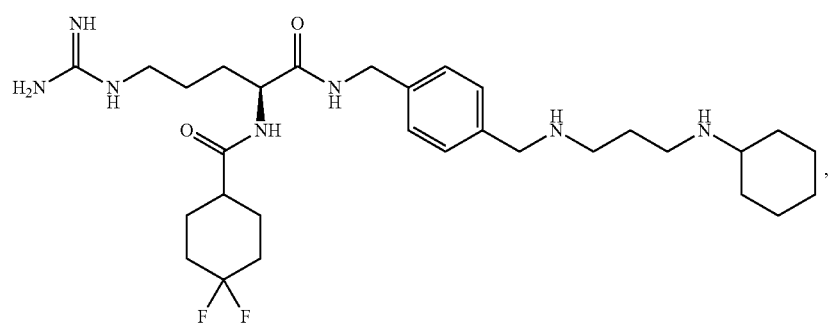
(7)

-continued
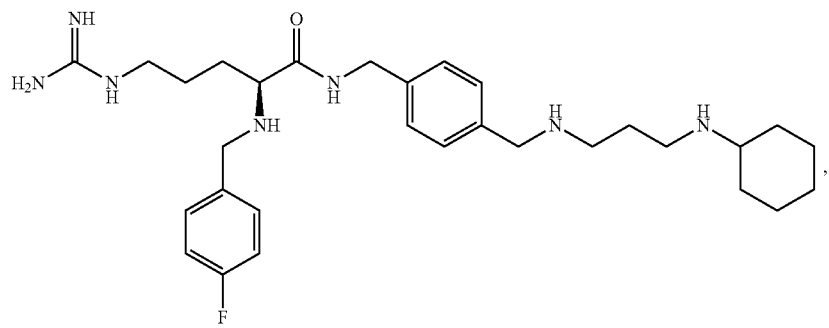
(8)
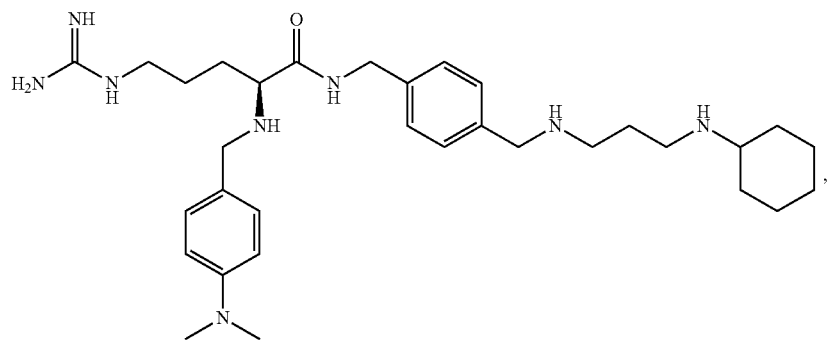
(9)
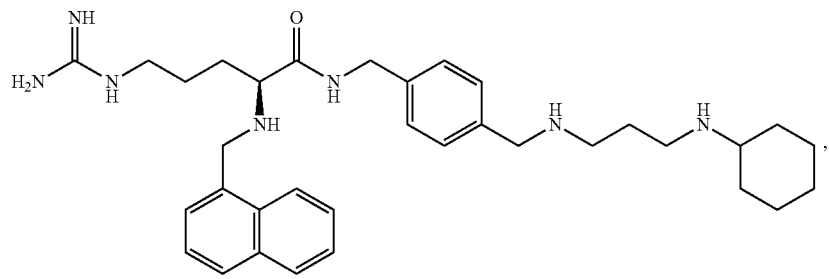
(10)
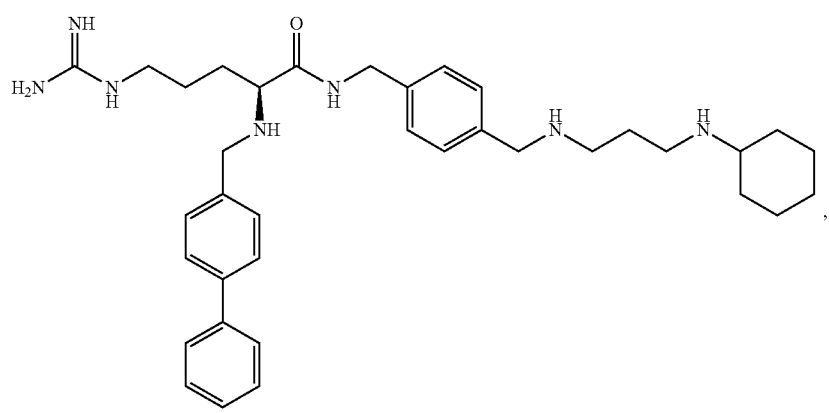
(11)
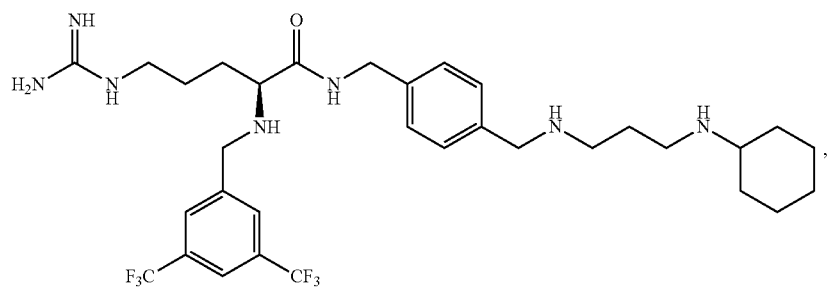
(12)

-continued
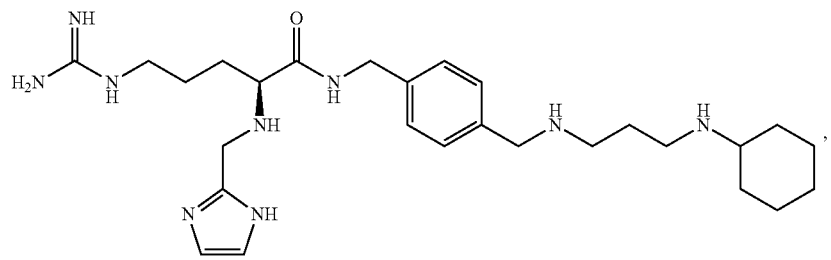
(13)
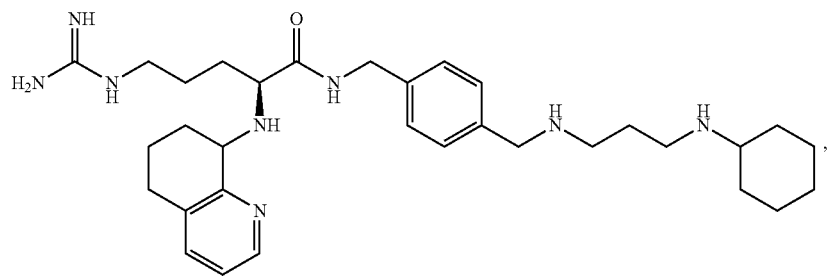
(14)
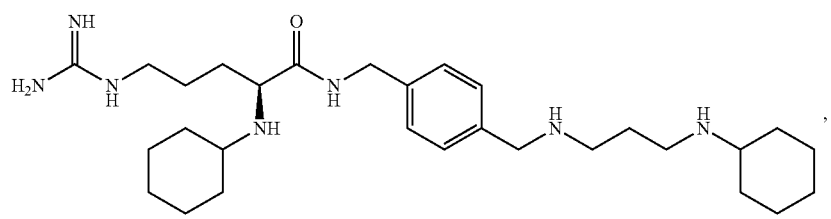
(15)
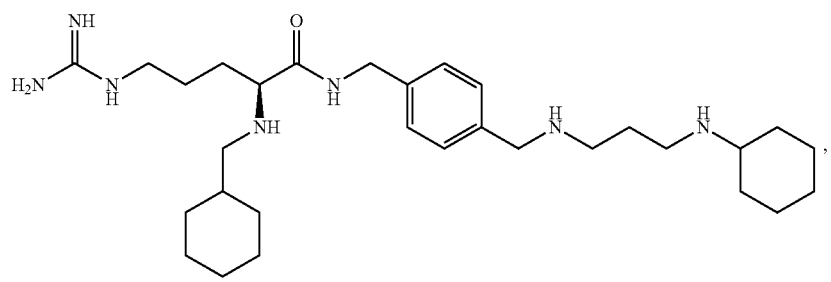
(16)
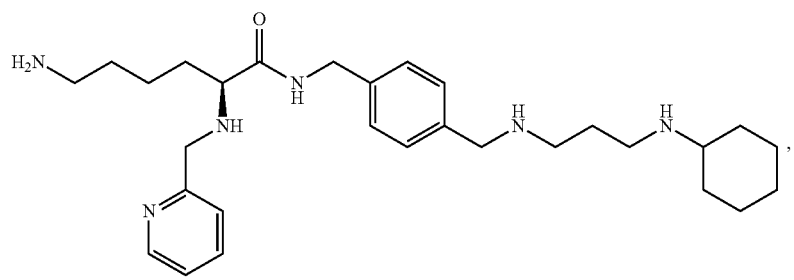
(17)
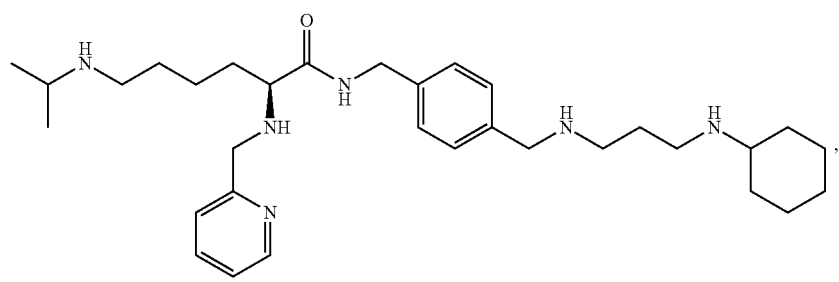
(18)

-continued
(19)
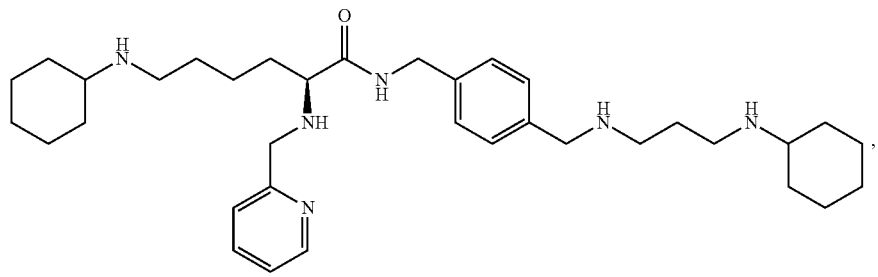
(20)
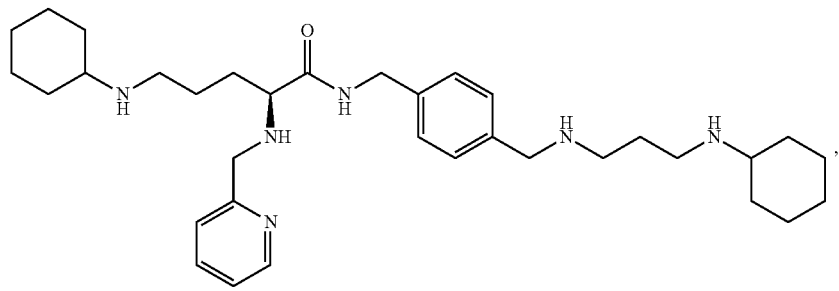
(21)
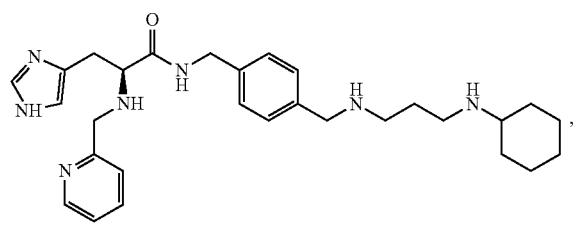
(22)
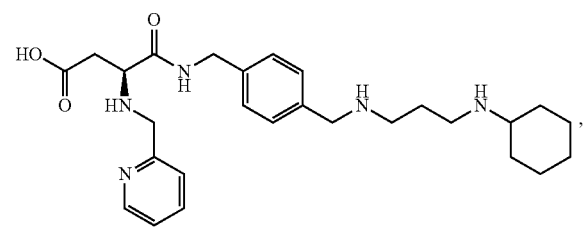
(23)
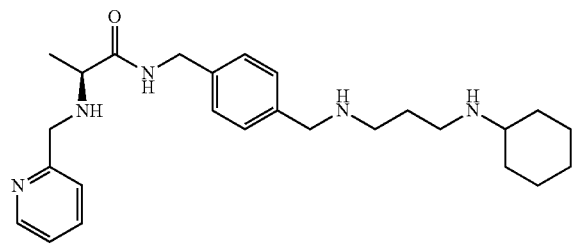 [SMILES: C[C@H](NCc1ccccn1)C(=O)NCc1ccc(CNCCCNC2CCCCC2)cc1]
(24)
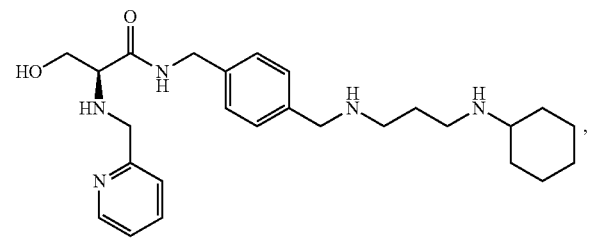
(25)
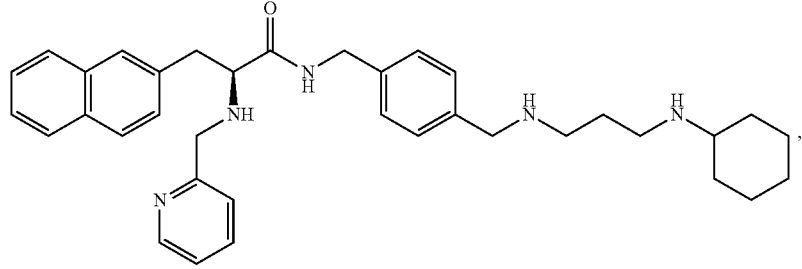
(26)
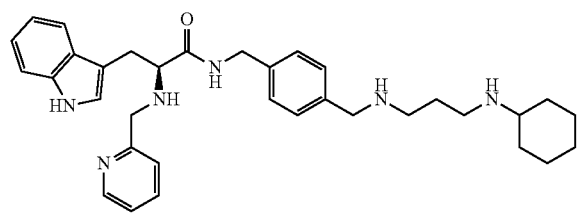 [SMILES: O=C(NCc1ccc(CNCCCNC2CCCCC2)cc1)[C@H](Cc1c[nH]c2ccccc12)NCc1ccccn1]
(27)
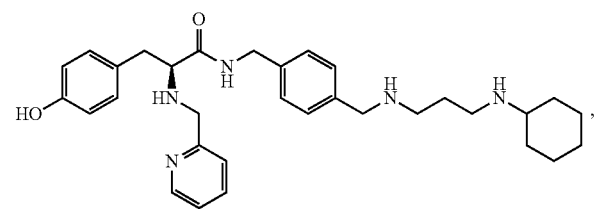

-continued

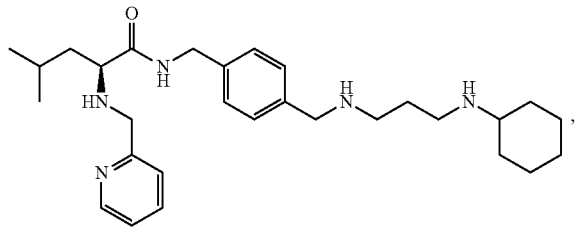

(28)

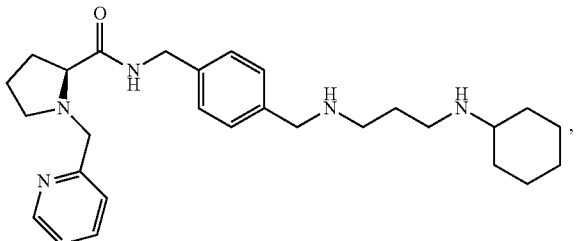

(29)

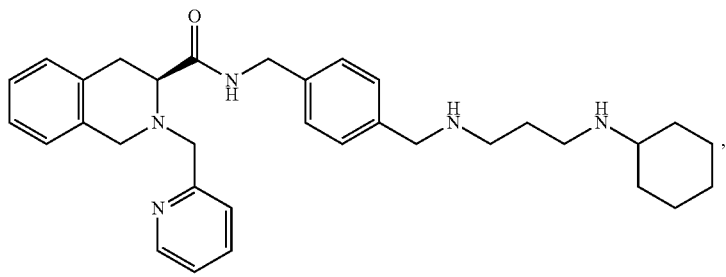

(30)

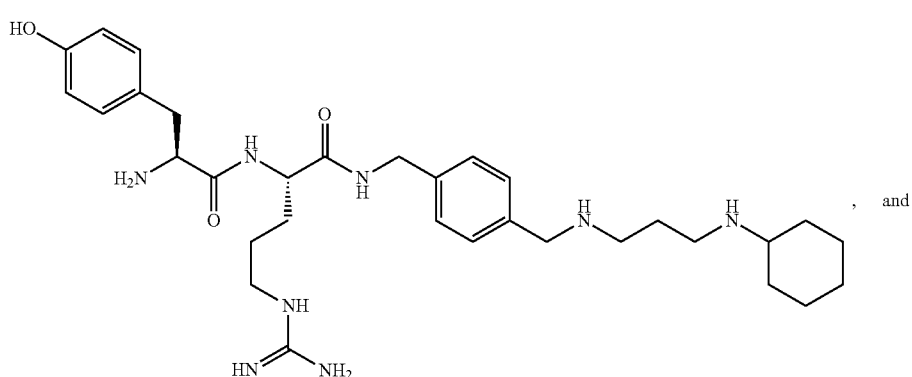

, and (31)

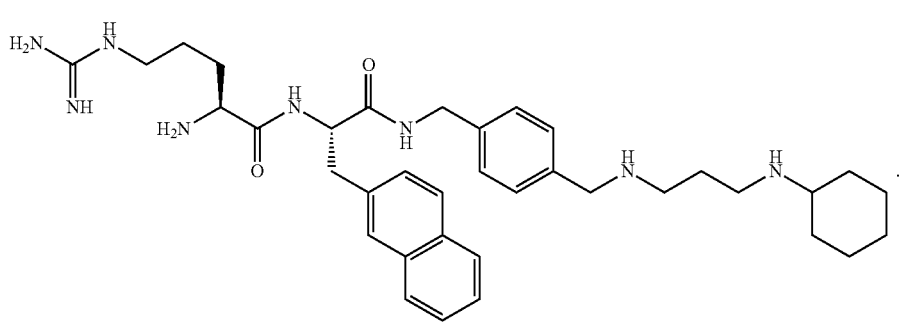

.

(32)

The compounds according to embodiments of the present disclosure have novel structure, are highly efficient and low-toxic, have excellent CXCR4 antagonistic activity, and are able to block HIV from invading and infecting human target cells, or treat or prevent AIDS, or mobilize human bone marrow hematopoietic cells, mesenchymal stem cells and stem cells, or interfere with cell migration and adhesion mediated by CXCL12/CXCR4, or prevent or treat tumor metastasis, invasion and growth mediated by CXCR4, or block autoimmune and inflammatory responses mediated by CXCL12/CXCR4. Moreover, the compounds according to embodiments of the present disclosure may be used as an active ingredient of a pharmaceutical composition for preventing or treating HIV in combination with other anti-HIV agents or for preventing or treating tumors in combination with other agents used for the treatment or prevention of leukemia, lymphoma, myeloma and solid tumor.

In a third aspect, the present disclosure provides use of a compound of formula (I) in preparation of a medicine. In some embodiments of the present disclosure, the medicine is used to inhibit interaction of a chemokine CXCL12 with a CXCR4 receptor or to inhibit the CXCR4 receptor. The compounds according to embodiments of the present disclosure are highly efficient and low-toxic, have excellent CXCR4 antagonistic activity, and are able to block HIV from invading and infecting human target cells, or treat or prevent AIDS, or mobilize human bone marrow hematopoietic cells, mesenchymal stem cells and stem cells, or interfere with cell migration and adhesion mediated by CXCL12/CXCR4, or prevent or treat tumor metastasis, invasion and growth mediated by CXCR4, or block autoimmune and inflammatory responses mediated by CXCL12/CXCR4.

In some embodiments of the present disclosure, the above-described use further includes at least one of the following additional technical features.

In an embodiment of the present disclosure, inhibiting the CXCR4 receptor is realized by antagonizing the CXCR4 receptor.

In an embodiment of the present disclosure, the medicine is used to block HIV from invading and infecting human target cells or to treat or prevent AIDS. The compound according to embodiments of the present disclosure or a salt or prodrug thereof can antagonize the CXCR4 receptor, block HIV from invading and infecting the human target cells, and may be used to the related research on anti-HIV lead pharmaceutical molecules and candidates.

In an embodiment of the present disclosure, the medicine is used to mobilize human bone marrow hematopoietic cells, mesenchymal stem cells or stem cells. The compound according to embodiments of the present disclosure or a salt or prodrug thereof can mobilize the human bone marrow hematopoietic cells and the mesenchymal stem cells, and may be used to the development and research of lead molecules of a stem cell mobilizer and candidates.

In an embodiment of the present disclosure, the medicine is used to interfere with CXCL12/CXCR4-mediated cell migration and adhesion.

In an embodiment of the present disclosure, the medicine is used to prevent or treat CXCR4-mediated tumor metastasis, invasion or growth. The compound according to embodiments of the present disclosure or a salt or prodrug thereof can interfere with CXCL12/CXCR4-mediated cell migration and adhesion, and may be used to prevent or treat CXCR4-mediated tumor metastasis, invasion or growth.

In an embodiment of the present disclosure, the medicine is used to block CXCL12/CXCR4-mediated autoimmune and inflammatory responses.

In an embodiment of the present disclosure, the medicine is used to prevent or treat an autoimmune or inflammatory disease. The compound according to embodiments of the present disclosure or a salt or prodrug thereof can block CXCL12/CXCR4-mediated autoimmune and inflammatory responses, and be used to prevent or treat the autoimmune and inflammatory diseases, as well as other diseases associated with the CXCR4 receptor.

In a fourth aspect, the present disclosure provides a pharmaceutical composition. In some embodiments of the present disclosure, the pharmaceutical composition includes the compound as described hereinbefore as an active ingredient. The pharmaceutical composition according to embodiments of the present disclosure is highly efficient and low-toxic, has excellent CXCR4 antagonistic activity, and can block HIV from invading and infecting human target cells, or treat or prevent AIDS, or mobilize human bone marrow hematopoietic cells, mesenchymal stem cells and stem cells, or interfere with cell migration and adhesion mediated by CXCL12/CXCR4, or prevent or treat tumor metastasis, invasion and growth mediated by CXCR4, or block autoimmune and inflammatory responses mediated by CXCL12/CXCR4, as well as can prevent or treat HIV, or prevent and treat leukemia, lymphoma, myeloma and other solid tumors.

According to embodiments of the present disclosure, the pharmaceutical composition further includes at least one of the following additional technical features.

In an embodiment of the present disclosure, the pharmaceutical composition further includes a pharmaceutically acceptable auxiliary.

In an embodiment of the present disclosure, the auxiliary includes a pharmaceutically acceptable excipient, lubricant, filler, diluent, disintegrant, stabilizer, preservative, emulsifier, cosolvent, colorant, sweetener well known in the formulation art for formulating the pharmaceutical composition into different dosage forms including tablets, pills, capsules, injections and the like.

In an embodiment of the present disclosure, the pharmaceutical composition further includes one or more other anti-HIV agents.

In an embodiment of the present disclosure, the one or more other anti-HIV agents include at least one selected form a group including maraviroc, enfuvirtide, zidovudine, zalcitabine, stavudine, lamivudine, nevirapine, delavirdine, abacavir, efavirenz, tenofovir, emtricitabine, etravirine, and rilpivirine. The compound according to embodiments of the present disclosure or a salt or prodrug thereof may be used in combination with at least one of the anti-HIV agents in different ratios for the prevention and treatment of AIDS.

In an embodiment of the present disclosure, the pharmaceutical composition further includes one or more other agents for the treatment or prevention of leukemia, lymphoma, myeloma and a solid tumor.

In an embodiment of the present disclosure, the one or more other agents for the treatment or prevention of leukemia, lymphoma, myeloma and the solid tumor include at least one selected form a group including cisplatin, cyclophosphamide, cytarabine, 5-fluorouracil, gemcitabine, taxol, docetaxel, adriamycin, glivec, tarceva, sorafenib, dasatinib, lapatinib, sunitinib, erlotinib, gefitinib, cetuximab, herceptin of trastuzumab. The compound according to embodiments of the present disclosure or a salt or prodrug thereof may be used in combination with at least one chemotherapeutic agent for the treatment of leukemia, lymphoma, myeloma and other solid tumors.

In a fifth aspect, the present disclosure provides a pharmaceutical nanocarrier. In some embodiments of the present disclosure, the pharmaceutical nanocarrier carries the compound as described hereinbefore and at least one other chemotherapeutic agent for treating cancer or anti-HIV agent. In some embodiments, the nanocarrier includes a biodegradable material well known in the field of medical delivery, such as liposome, solid lipid, albumin, gelatin, dextran, chitosan, hydrogel, polymeric micelles, polyalkylcyanoacrylate, polylactic acid-polyglycolic acid copolymer. The pharmaceutical nanocarrier according to embodiments of the present disclosure is highly efficient and low-toxic, has excellent CXCR4 antagonistic activity, and can block HIV from invading and infecting human target cells, or treat or prevent AIDS, or mobilize human bone marrow hematopoietic cells, mesenchymal stem cells and stem cells, or interfere with cell migration and adhesion mediated by CXCL12/CXCR4, or prevent or treat tumor metastasis, invasion and growth mediated by CXCR4, or block autoimmune and inflammatory responses mediated by CXCL12/CXCR4, as well as can prevent or treat HIV, or prevent and treat leukemia, lymphoma, myeloma and other solid tumors.

In a sixth aspect, the present disclosure provides a method for treating an autoimmune disease, an inflammatory disease, cancer or HIV. In some embodiments of the present disclosure, the method includes: administering to a patient the compound or the pharmaceutical composition as described hereinbefore.

In some embodiments of the present disclosure, the method further includes at least one of the following additional technical features.

In an embodiment of the present disclosure, the cancer includes leukemia, lymphoma, myeloma and a solid tumor.

The term "administering/administration to a patient the compound or the pharmaceutical composition as described hereinbefore" as used herein refers to introducing a predetermined amount of a substance into the patient in a suitable manner. The compound of formula (I) or the pharmaceutical composition according to embodiments of the present disclosure may be administered via any conventional route as long as it can reach a desired tissue. Various routes of administration are contemplated, including but not limited to peritoneal, intravenous, muscular, subcutaneous, cortical, oral, local, nasal, pulmonary and rectal administrations. However, for the oral administration, the composition should be coated or formulated to prevent its active component from degrading in the stomach. Preferably, the compound of formula (I) or the pharmaceutical composition of the present disclosure may be administered in an injectable preparation. Further, the compound of formula (I) or the pharmaceutical composition of the present disclosure may be administrated using a specific device for delivering the active ingredient to target cells.

The frequency and amount of administration of the pharmaceutical composition of the present disclosure may be determined according to several relevant factors, including the type of the disease to be treated, the route of administration, the age, sex, and weight of a patient, the severity of the disease, as well as the type of the medicine as the active ingredient. According to some embodiments of the present disclosure, the daily dosage may be divided into 1, 2 or multiple doses in an appropriate form for administration once, twice or several times in the whole time period, provided that a therapeutically effective amount is reached.

The term "therapeutically effective amount" refers to an amount of a compound that is enough to significantly ameliorate certain symptoms associated with a disease or disorder, i.e., an amount that provides a therapeutic effect for a given disorder and dosage regimen. For example, in the treatment of HIV, a medicine or compound that reduces, prevents, delays, inhibits or blocks any symptoms of the disease or disorder should be considered as effective. A therapeutically effective amount of medicine or compound is not required to cure a disease or disorder, but will provide treatment for the disease or disorder, such that the onset of the disease or disorder of an individual is delayed, stopped or prevented, or the symptoms of the disease or disorder are alleviated, or the duration of the disease or disorder is altered, or for example, the disease or disorder becomes less serious, or the recovery is accelerated.

The terms "treating", "treat" or "treatment" refer to achievement of desired pharmacological and/or physiological effects. The effects may be prophylactic in terms of the complete or partial prevention of the disease or its symptoms, and/or may be therapeutic in terms of the partial or complete cure of the disease and/or adverse effects caused by the disease. The terms "treating", "treat" or "treatment" used herein cover the treatment of diseases (mainly including an autoimmune or inflammatory disease, cancer or HIV) in mammals, especially in humans, including: (a) prevention the occurrence of diseases (such as autoimmune or inflammatory diseases, leukemia, lymphoma, myeloma or solid tumor) or disorders in individuals who are susceptible to diseases but have not yet been diagnosed; (b) inhibition the development of diseases such as autoimmune or inflammatory disease, leukemia, lymphoma, myeloma, solid tumor or HIV; or (c) alleviation of diseases or symptoms associated therewith. Further, the terms "treating", "treat" and "treatment" used herein cover any administration of a medicine or compound to an individual to treat, cure, alleviate, ameliorate, relieve or inhibit a disease in the individual, including but not limited to administration of an agent containing the compound of formula (I) or the pharmaceutical composition as described herein to an individual in need.

In yet another aspect, the present disclosure further provides design approaches, synthesis schemes, and preparation methods of the compound of formula (I). According to embodiments of the present disclosure, the design approaches are to assemble the structural segments to different amino acid skeletons as described above at a C-terminal or a N-terminal of the amino acids. Through different synthesis schemes, a series of hybrid peptide molecules with different amino acid skeletons are obtained. The exemplified compounds provided herein (their chemical structural formulas are shown in Table 1) are explanatory, and shall not be construed to limit the present disclosure. According to some embodiments of the present disclosure, the exemplified compounds provided herein may be prepared in accordance with the following synthesis schemes (1), (2) and (3).

According to embodiments of the present disclosure, the synthesis scheme (1) of intermediates is as follows: as a starting material, p-cyanobenzaldehyde is firstly subjected to reductive amination with N-(3-aminopropyl) cyclohexylamine to obtain an intermediate 1-1a or 1-1b, which is then subjected to Boc protection to give an intermediate 1-2a or 1-2b, finally, the intermediate 1-2a or 1-2b is reduced to obtain a critical intermediate 1-3a or 1-3b.

synthesis scheme (1) of intermediates

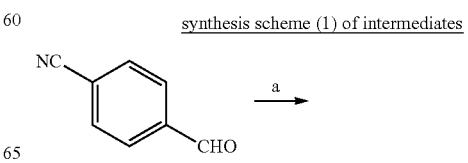

-continued

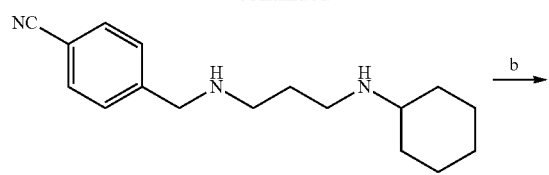

1-1a

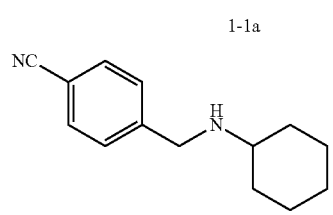

1-1b

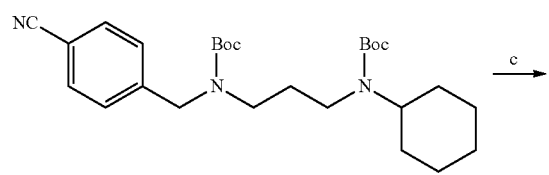

1-2a

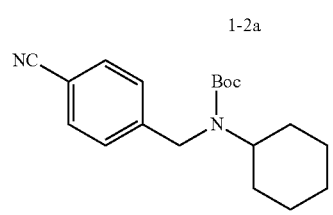

1-2b

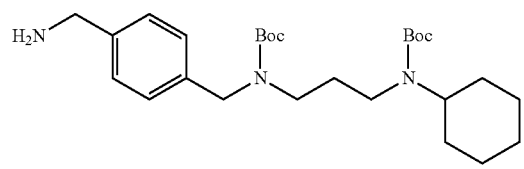

1-3a

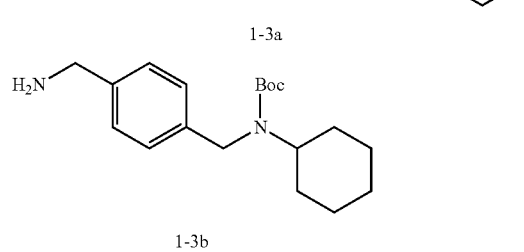

1-3b

According to embodiments of the present disclosure, the synthesis scheme (2) of non-natural amino acids is as follows: an amino acid which is commercially available as the raw material is successively subjected to Boc deprotection and reductive amination to obtain an intermediate 2-2a, 2-2b or 2-2c, which is then subjected to Boc protection to obtain a corresponding non-natural amino acid intermediate 2-3a, 2-3b or 2-3c.

synthesis scheme (2) of non-natural amino acids

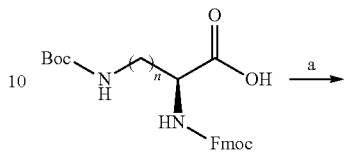

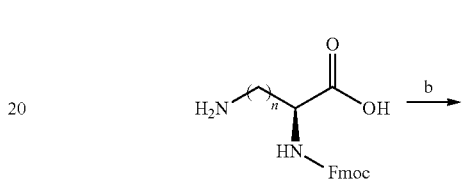

2-1a, n = 4
2-1b, n = 3

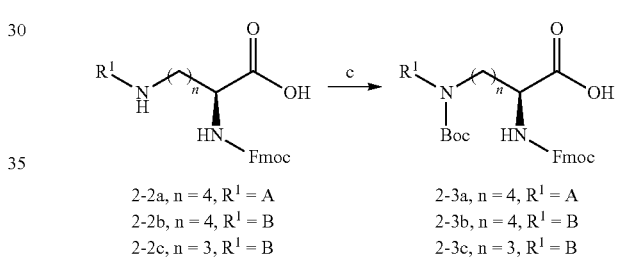

2-2a, n = 4, R¹ = A      2-3a, n = 4, R¹ = A
2-2b, n = 4, R¹ = B      2-3b, n = 4, R¹ = B
2-2c, n = 3, R¹ = B      2-3c, n = 3, R¹ = B

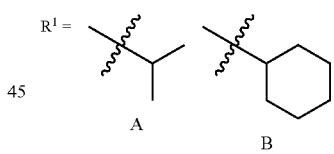

According to embodiments of the present disclosure, the synthesis scheme (3) of target compounds is as follows: an amino acid which is synthesized or commercially available as the raw material is subjected to a condensation reaction with the intermediate 1-3a or 1-3b to obtain an intermediate 3-1, which is then subjected to Fmo deprotection to obtain a critical intermediate 3-2. On the one hand, the intermediate 3-2 may be subjected to reductive amination with a raw material or intermediate containing an aldehyde group or a ketone group to obtain an intermediate 3-3, which is then subjected to Boc deprotection to obtain the target compound; on the other hand, the intermediate 3-2 may be subjected to a condensation reaction with a raw material or intermediate containing a carboxyl group or with any amino acid to obtain an intermediate 3-4, which is then subjected to Boc deprotection to obtain the target compound.

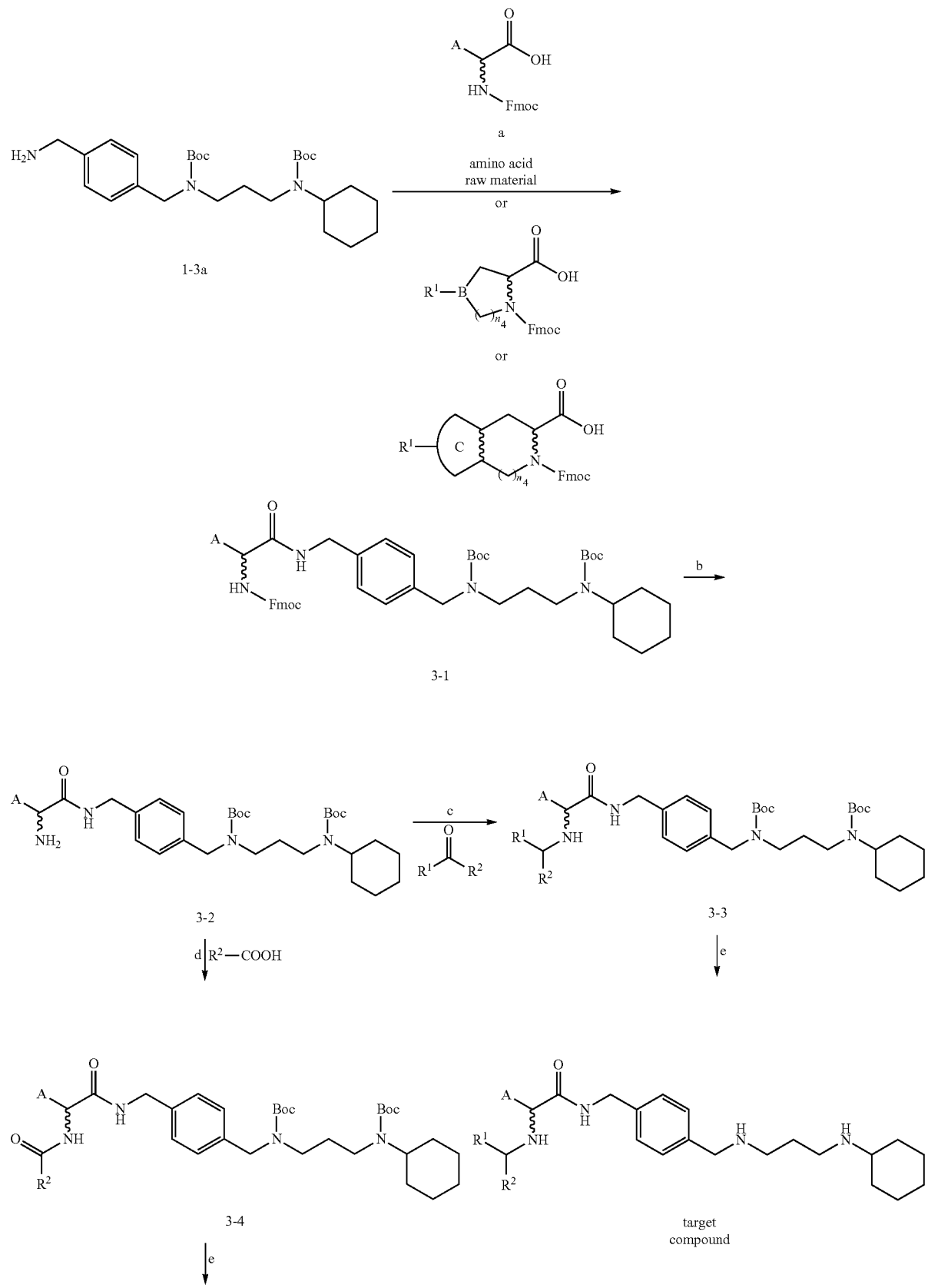
synthesis scheme (3) of target compounds

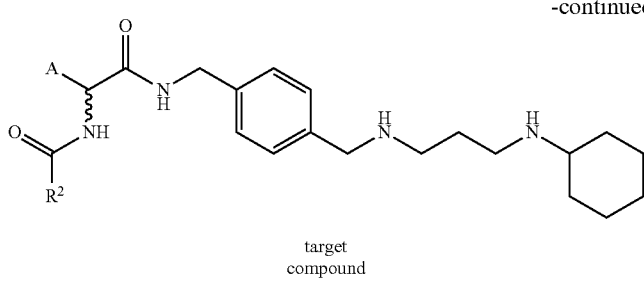

target compound

It is to be understood that, the preparation of the compounds according to embodiments of the present disclosure is not limited to the above synthesis schemes, and the organic synthesis reactions involved therein are basic chemical reactions which are well known to and may be mastered after learning by those skilled in the art. It is further to be understood that the compounds according to the present disclosure may be prepared in accordance with other synthesis schemes by changing reaction materials and reaction types.

In yet another aspect of the present disclosure, a series of in vitro bioactive assays were performed, such as cytotoxicity assay, binding affinity assay of CXCR4, chemotaxis assay, and intracellular calcium mobilization assay, which confirm the low toxicity and excellent CXCR4 antagonistic activity of the exemplified compounds. The compound according to embodiments of the present disclosure is in a free form or in a form of a salt or prodrug thereof, which can inhibit the interaction of the chemokine CXCL12 with the CXCR4 receptor, exhibit the CXCR4 receptor antagonistic activity, and may be used as an effective ingredient of the CXCR4 antagonist.

According to embodiments of the present disclosure, prodrug forms of the compounds of formula (I) include derivatives selected from carboxylates, phosphates, and borates, which are metabolized in vivo to original forms of the above compounds to exert pharmacological effects.

DETAILED DESCRIPTION

Figure 1:
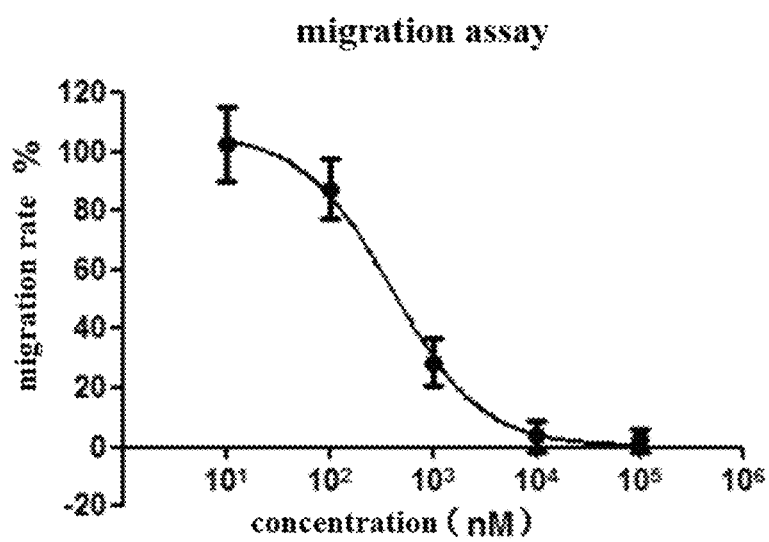
FIG. 1 is a graph showing experimental results of the inhibition of CXCR4 induced cell migration by compound 1 according to an embodiment of the present disclosure.

Examples of the present disclosure will be described in details below, which are exemplary and intended to explain the present disclosure, and shall not be construed to limit the present disclosure.

Example 1: Preparation of the Intermediate 1-3a: Refer to the Synthesis Scheme (1)

4-cyanobenzaldehyde (10 g) was dissolved in methanol (150 ml), to the obtained solution were added with N-(3-aminopropyl) cyclohexylamine (12.4 mL) and a suitable amount of 4 Å molecular sieves, and then the solution was heated to 65° C. and stirred for 6 hours. After cooled to the room temperature, the solution was added with sodium borohydride (5.8 g) in portions and stirred at room temperature for 1 to 2 hours. The reaction was quenched with a saturated ammonium chloride solution, and the solution was concentrated to dryness. The residue was ultrasonically washed with methanol and then filtered. The filtrate was collected and evaporated to dryness to obtain the intermediate 1-1a crude product for use in the next reaction directly.

The above crude intermediate 1-1a was directly dissolved in tert-butanol (100 ml) and sodium carbonate solution (2 mol/L, 100 ml), and then added with $Boc_2O$ (40 g) in portions. The resulted solution was stirred overnight at room temperature, and then diluted with an appropriate amount of water, followed by extracted with ethyl acetate. The combined organic layer was washed with a saturated sodium chloride solution, and dried with anhydrous sodium sulfate as well as by rotary evaporation to obtain a residue. The residue was purified by silica gel column chromatography to obtain the intermediate 1-2a (22 g, yield: 63%).

7 g of the above intermediate 1-2a was weighed and dissolved in methanol (50 ml) and tetrahydrofuran (50 ml), followed by sequential addition of Raney Ni (wet weight, 2 g) and aqueous ammonia (2 mL) in nitrogen atmosphere, and then the nitrogen was replaced with hydrogen. The solution was stirred overnight in hydrogen atmosphere, and then filtered by diatomite pad. The filtrate was evaporated to dryness, and the residue obtained thereby is the intermediate 1-3a (6 g, yield: 85%), ESI-MS: $[M+1]^+$476.8.

Example 2: Preparation of the Intermediate 1-3b

Referring to the synthesis scheme (1), the synthetic processes and conditions for the preparation of the intermediate 1-3b are similar to that of the intermediate 1-3a.

Example 3: Preparation of the Intermediate 2-3a: Refer to the Synthesis Scheme (2)

5 g of amino acid raw material, Fmoc-L-Lys(Boc)-OH, was weighted and suspended in dichloromethane (40 ml), and then added with trifluoroacetic acid (20 ml). The obtained solution was stirred at room temperature for 1 to 2 hours, and then dried by rotary evaporation. The residue was precipitated with ice diethyl ether to obtain a white precipitate (i.e., the intermediate 2-1a), which was directly dissolved in methanol (50 ml), and then added with acetone (20 ml) and trifluoroacetic acid (2 ml). The resulted solution, after stirred at room temperature for 2 hours, was added with sodium triacetoxyborohydride (11.3 g) and then stirred overnight. Finally, the solution was adjusted to a pH of 4 to 6 with a hydrochloric acid solution (4 mol/L), and then concentrated to a certain volume, followed by extracted with ethyl acetate. The combined organic phase was dried with anhydrous sodium sulfate and then filtered. The filtrate was dried by rotary evaporation to obtain a residue (i.e., a crude product of the intermediate 2-2a) for use in the next reaction directly.

The above obtained intermediate 2-2a was dissolved in tert-butanol (50 mL) and sodium carbonate solution (2 mol/L, 20 mL), and then added with $Boc_2O$ (32 g) in portions. The solution was stirred overnight at room temperature, and then diluted with water, followed by extracted with ethyl acetate. The combined organic phase was washed with saturated sodium chloride solution, dried with anhydrous sodium sulfate, and then filtered. The filtrate was dried by rotary evaporation, and the resulted residue was purified by silica gel column chromatography to obtain the intermediate 2-3a (3.35 g, yield: 61%), MALDI-TOF-MS $[M+Na]^+$: 533.2587

Example 4: Preparation of the Intermediate 2-3b

Referring to the synthesis scheme (2), the synthetic processes and conditions for the preparation of the intermediate 2-3b are similar to that of the intermediate 2-3a. MALDI-TOF-MS: $[M+Na]^+$ 573.3250.

Example 5: Preparation of the Intermediate 2-3c

Referring to the synthesis scheme (2), the synthetic processes and conditions for the preparation of the intermediate 2-3c are similar to that of the intermediate 2-3a. MALDI-TOF-MS: $[M+Na]^+$ 559.3325.

Example 6: Preparation of Compound 1: Refer to the Synthesis Scheme (3)

Preparation of the intermediate 3-1: the intermediate 1-3a (3.20 g) and an amino acid raw material Fmoc-Arg(Pbf)-OH (4.58 g) were weighted and dissolved in DMF (50 ml), followed by addition of HATU (3.84 g), HOBt (0.91 g), and DIPEA (2.22 mL) successively. The resulted solution was stirred overnight at room temperature, and then added dropwise to water to form precipitates, which were collected and dried in vacuum to obtain a solid product (i.e., the intermediate 3-1) for use in the next reaction directly.

Preparation of the intermediate 3-2: the above obtained intermediate 3-1 was directly dissolved in DMF (56 ml) and piperidine (14 ml), and stirred at room temperature for 1 to 2 hours. Then, the solution was diluted with a saturated sodium chloride solution, and extracted with ethyl acetate. The combined organic phase was washed with a saturated sodium chloride solution, dried with anhydrous sodium sulfate, and then filtered. The filtrate was dried by rotary evaporation, and the obtained residue was purified by silica gel column chromatography to obtain a semisolid, i.e., the intermediate 3-2 (4.3 g, yield: 72%), HR-MS: $[M+Na]^+$ 906.5131.

Preparation of the intermediate 3-3: the above prepared intermediate 3-2 (200 mg) was weighted and dissolved in anhydrous methanol (5 ml), and then added with 2-pyridyl formaldehyde (0.023 mL) and acetic acid (0.010 ml). The resulted solution was stirred at room temperature for 2 hours, and then added with sodium triacetoxyborohydride (146 mg) to continue react overnight at room temperature. Finally, the solution was quenched with a saturated sodium carbonate solution and extracted with ethyl acetate. The combined organic phase was dried with anhydrous sodium sulfate, and then filtered. The filtrate was dried by rotary evaporation, and the obtained residue was purified by silica gel column chromatography to obtain an oily substance (i.e., the intermediate 3-3) for use in the next reaction directly.

Preparation of target compound 1: the above prepared intermediate 3-3 was dissolved in a deprotection solution (trifluoroacetic acid:triisopropylsilane:water=95:2.5:2.5) to react for 2 hours at room temperature. The reaction solution, after removal of solvents therefrom, was precipitated and washed with ice diethyl ether. The collected solid was purified by reversed-phase medium pressure preparative chromatography to obtain trifluoroacetate of the compound 1 (45 mg).

$^1$H NMR (400 MHz, DMSO-$d_6$) δ 9.58; (br, 2H), 9.31; (s, 2H), 9.18; (t, J=5.5 Hz, 1H), 8.77; (br-s, 2H), 8.63; (d, J=4.7 Hz, 1H), 8.07; (d, J=4.5 Hz, 1H), 7.89; (t, J=7.7 Hz, 1H), 7.49-33; (m, 9H), 4.46; (dd, J=15.4, 6.0 Hz, 1H), 4.32; (dd, J=15.5, 5.2 Hz, 1H), 4.27; (br-s, 2H), 4.14; (s, 2H), 3.96; (t, J=6.0 Hz, 1H), 3.13; (dd, J=12.4, 6.2 Hz, 2H), 3.00; (br-s, 5H), 2.08-1.81; (m, 6H), 1.78-1.70; (m, 2H), 1.61-1.46; (m, 3H), 1.30-1.18; (m, 4H), 1.13-1.03; (m, 1H).

$^1$H NMR (400 MHz, DMSO-$d_6$+$D_2O$) δ 9.17; (t, J=5.7 Hz, 1H), 8.62; (d, J=4.5 Hz, 1H), 7.88; (td, J=7.7, 1.4 Hz, 1H), 7.48-7.42; (m, 4H), 7.33; (d, J=8.0 Hz, 2H), 4.44; (d, J=15.5 Hz, 1H), 4.31; (d, J=15.4 Hz, 1H), 4.26; (s, 2H), 4.13; (s, 2H), 3.12; (t, J=6.8 Hz, 2H), 3.06-2.89; (m, 5H), 2.05-1.82; (m, 6H), 1.77; (m, 2H), 1.64-1.42; (m, 3H), 1.32-1.15; (m, 4H), 1.15-1.02; (m, 1H). HRMS (ESI, m/z): $[M+H]^+$ 523.3883.

Example 7: Preparation of Compound 2: Refer to the Synthesis Scheme (3)

Preparation of the intermediate 3-4: the above prepared intermediate 3-2 (200 mg) and p-fluorobenzoic acid (39 mg) were weighted and dissolved in DMF (4 ml), followed by addition of HATU (131 g), HOBt (31 g), and DIPEA (0.076 mL) successively. The resulted solution was stirred overnight at room temperature, and then added dropwise to water to form precipitates, which were collected and dried in vacuum to obtain a solid product (i.e., the intermediate 3-4) for use in the next reaction directly.

Preparation of target compound 2: the above prepared intermediate 3-4 was dissolved directly in a deprotection solution (trifluoroacetic acid:triisopropylsilane:water=95: 2.5:2.5) to react for 2 hours at room temperature. The reaction solution, after removal of solvents therefrom, was precipitated and washed with ice diethyl ether. The collected solid was purified by reversed-phase medium pressure preparative chromatography to obtain trifluoroacetate of the compound 2 (145 mg).

$^1$H NMR (400 MHz, DMSO-$d_6$) (δ 9.15 (br-s, 2H), 8.69; (br-s, 2H), 8.60; (dd, J=12.3, 6.8 Hz, 2H), 8.00; (dd, J=8.3, 5.8 Hz, 2H), 7.79; (br-s, 1H), 7.68-6.86; (m, 10H), 4.45; (dd, J=13.3, 8.7 Hz, 1H), 4.31; (qd, J=15.7, 6.0 Hz, 2H), 4.12; (br-s, 2H), 3.12; (dd, J=12.5, 6.4 Hz, 2H), 2.99; (br-s, 5H), 2.07-1.87; (m, 4H), 1.90-1.81; (m, 1H), 1.84-1.66; (m, 3H), 1.62-1.46; (m, 3H), 1.30-1.18; (m, 4H), 1.15-1.03; (m, 1H).

$^1$H NMR (400 MHz, DMSO-$d_6$+$D_2O$) δ 7.99-7.96; (m, 1H), 7.40; (d, J=8.2 Hz, 2H), 7.31-7.27; (m, 4H), 4.44; (dd, J=9.7, 5.0 Hz, 1H), 4.30; (q, J=15.7 Hz, 2H), 4.11; (s, 2H), 3.11; (t, J=7.0 Hz, 1H), 3.01-2.89; (m, 2H), 1.97-1.92; (m, 4H), 1.87-1.78; (m, 1H), 1.75-1.69; (m, 3H), 1.62-1.46; (m, 3H), 1.29-1.17; (m, 2H), 1.12-1.04; (m, 1H). HRMS (ESI, m/z): $[M+H]^+$ 554.3613.

Example 8: Preparation of Compound 3

Referring to the synthesis scheme (3), except that the intermediate 1-3a was replaced with benzylamine, the remaining synthetic processes and conditions for the preparation of compound 3 were similar to that of compound 1.

$^1$H NMR (400 MHz, D$_2$O) (δ 8.64; (d, J=5.6 Hz, 1H), 8.42; (t, J=7.9 Hz, 1H), 8.00; (d, J=8.0 Hz, 1H), 7.97-7.84; (m, 1H), 7.25-7.13; (m, 5H), 4.58; (d, J=14.3 Hz, 1H), 4.43; (d, J=14.3 Hz, 1H), 4.30; (d, J=14.7 Hz, 1H), 4.12; (d, J=14.7 Hz, 1H), 4.03; (dd, J=7.6, 5.3 Hz, 1H), 2.94; (t, J=6.9 Hz, 2H), 1.88-1.77; (m, 2H), 1.40-1.28; (m, 2H). HRMS (ESI, m/z): [M+H]$^+$355.2254.

Example 9: Preparation of Compound 4

Referring to the synthesis scheme (3), except that the intermediate 1-3a was replaced with the intermediate 1-3b, the remaining synthetic processes and conditions for the preparation of compound 4 were similar to that of compound 1.

$^1$H NMR (400 MHz, D$_2$O) (δ 8.76; (d, J=5.5 Hz, 1H), 8.50; (t, J=7.8 Hz, 1H), 8.06; (d, J=8.0 Hz, 1H), 7.98; (t, J=6.7 Hz, 1H), 7.38; (d, J=7.8 Hz, 2H), 7.31; (d, J=7.9 Hz, 2H), 4.64; (d, J=14.3 Hz, 1H), 4.51; (d, J=14.3 Hz, 1H), 4.42; (d, J=15.0 Hz, 1H), 4.31; (d, J=15.0 Hz, 1H), 4.20-4.07; (m, 3H), 3.15-3.02; (m, 3H), 2.08-2.02; (m, 2H), 2.00-1.90; (m, 2H), 1.76; (d, J=12.4 Hz, 2H), 1.60-1.46; (m, 3H), 1.34-1.17; (m, 4H), 1.14-1.03; (m, 1H). HRMS (ESI, m/z): [M+H]$^+$466.3289.

Example 10: Preparation of Compound 5

The intermediate 3-2 (200 mg) mentioned in the synthesis scheme (3) was weighted and dissolved directly in a deprotection solution (trifluoroacetic acid:triisopropylsilane:water=95:2.5:2.5) to react for 2 hours at room temperature. The reaction solution, after removal of solvents therefrom, was precipitated and washed with ice diethyl ether. The collected solid was purified by reversed-phase medium pressure preparative chromatography to obtain trifluoroacetate of the compound 5 (145 mg).

$^1$H NMR (400 MHz, DMSO-d$_6$) δ 9.31; (br-s, 2H), 9.08; (t, J=5.6 Hz, 1H), 8.78; (br-s, 2H), 8.30; (br-s, 3H), 8.05; (s, 1H), 7.45; (d, J=8.1 Hz, 4H), 7.33; (d, J=8.0 Hz, 4H), 4.43; (dd, J=15.5, 6.1 Hz, 1H), 4.31; (dd, J=15.5, 5.4 Hz, 1H), 4.14; (br-s, 2H), 3.85; (d, J=5.0 Hz, 1H), 3.12; (dd, J=12.7, 6.5 Hz, 2H), 3.00; (br-s, 5H), 2.02-1.96; (m, 4H), 1.78-1.72; (m, 4H), 1.61-1.46; (m, 3H), 1.30-1.17; (m, 4H), 1.13-1.07; (m, 1H). HRMS (ESI, m/z): [M+H]$^+$432.3431.

Example 11: Preparation of Compound 6

Referring to the synthesis scheme (3), except that the Fmoc-Arg(Pbf)-OH was replaced with an amino acid raw material Fmoc-D-Arg(Pbf)-OH, the remaining synthetic processes and conditions for the preparation of compound 6 were similar to that of compound 1.

$^1$H NMR (400 MHz, D$_2$O) δ 8.73; (d, J=5.5 Hz, 1H), 8.47; (t, J=7.9 Hz, 1H), 8.03; (d, J=8.0 Hz, 1H), 7.99-7.92; (m, 1H), 7.36; (d, J=8.0 Hz, 2H), 7.30; (d, J=8.0 Hz, 2H), 4.55; (dd, J=51.9, 14.3 Hz, 2H), 4.35; (dd, J=38.7, 15.1 Hz, 2H), 4.15; (br-s, 2H), 4.13-4.07; (m, 1H), 3.10-2.95; (m, 7H), 2.03-1.89; (m, 6H), 1.72; (br-s, 2H), 1.56-1.43; (m, 3H), 1.26-1.43; (m, 4H), 1.10-1.04; (m, 1H). HRMS (ESI, m/z): [M+H]$^+$523.3870.

Example 12: Preparation of Compound 7

Referring to the synthesis scheme (3), except that p-fluorobenzoic acid was replaced with 4,4-difluorocyclohexanecarboxylic acid, the remaining synthetic processes and conditions for the preparation of compound 7 were similar to that of compound 2.

$^1$H NMR (400 MHz, DMSO-d$_6$) δ 9.12; (br-s, 2H), 8.65; (br-s, 2H), 8.50; (t, J=6.0 Hz, 1H), 8.12; (d, J=8.0 Hz, 1H), 7.76; (t, J=5.4 Hz, 1H), 7.41; (d, J=8.0 Hz, 2H), 7.28; (d, J=8.0 Hz, 2H), 7.30-6.95; (m, 4H), 4.36-4.31; (m, 1H), 4.27-4.22; (m, 2H), 4.13; (br-s, 2H), 3.11-3.06; (m, 2H), 2.99; (br-s, 5H), 2.41-2.35; (m, 1H), 2.08-1.92; (m, 6H), 1.85-1.66; (m, 7H), 1.64-1.43; (m, 6H), 1.29-1.18; (m, 4H), 1.14-1.06; (m, 1H). HRMS (ESI, m/z): [M+H]$^+$578.3994.

Example 13: Preparation of Compound 8

The synthetic processes and conditions for the preparation of compound 8 were similar to that of compound 1.

$^1$H NMR (400 MHz, DMSO-d$_6$) δ 9.45; (br., 2H), 9.28; (s, 2H), 9.21; (t, J=5.6 Hz, 1H), 8.74; (br-s, 2H), 8.05; (s, 1H), 7.66-7.20; (m, 11H), 4.44; (dd, J=15.3, 5.9 Hz, 1H), 4.32; (dd, J=15.3, 5.3 Hz, 1H), 4.14-4.02; (m, 4H), 3.79; (br-s, 1H), 3.11; (dd, J=12.6, 6.4 Hz, 2H), 2.99; (br-s, 5H), 1.97; (br-s, 4H), 1.92-1.67; (m, 4H), 1.66-1.35; (m, 3H), 1.28-1.17; (m, 4H), 1.15-1.05; (m, 1H). HRMS (ESI, m/z): [M+H]$^+$540.3826.

Example 14: Preparation of Compound 9

The synthetic processes and conditions for the preparation of compound 9 were similar to that of compound 1.

$^1$H NMR (400 MHz, D$_2$O) δ 7.58; (q, J=8.5 Hz, 4H), 7.39; (d, J=7.7 Hz, 2H), 7.33; (d, J=7.8 Hz, 2H), 4.41-4.29; (m, 2H), 4.24-4.10; (m, 4H), 3.90; (t, J=6.5 Hz, 1H), 3.24-3.18; (m, 6H), 3.12-3.01; (m, 7H), 2.05-1.94; (m, 4H), 1.91-1.84; (m, 2H), 1.74; (br-s, 2H), 1.58-1.40; (m, 3H), 1.28-1.16; (m, 2H), 1.14-1.01; (m, 1H). HRMS (ESI, m/z): [M+H]$^+$ 565.4337.

Example 15: Preparation of Compound 10

The synthetic processes and conditions for the preparation of compound 10 were similar to that of compound 1.

$^1$H NMR (400 MHz, DMSO-d$_6$) δ 9.60; (br-s, 1H), 9.35; (br-s, 1H), 9.27; (br-s, 2H), 8.74; (br-s, 2H), 8.14; (d, J=8.1 Hz, 1H), 8.12-7.99; (m, 3H), 7.68-7.55; (m, 4H), 7.52-7.06; (m, 7H), 4.61-4.37; (m, 4H), 4.13; (br-s, 2H), 4.06; (br-s, 1H), 3.15-3.10; (m, 2H), 2.98; (br-s, 5H), 2.07-1.80; (m, 6H), 1.75; (br-s, 2H), 1.61-1.50; (m, 3H), 1.29-1.1.17; (m, 4H), 1.15-1.06; (m, 1H). HRMS (ESI, m/z): [M+H]$^+$ 572.4095.

Example 16: Preparation of Compound 11

The synthetic processes and conditions for the preparation of compound 11 were similar to that of compound 1.

$^1$H NMR (400 MHz, DMSO-d$_6$) (δ 9.52; (br-s, 2H), 9.29-9.22; (m, 3H), 8.75; (br-s, 2H), 8.07; (t, J=5.7 Hz, 1H), 7.77-7.67; (m, 4H), 7.59-7.45; (m, 7H), 7.44-7.12; (m, 5H), 4.46; (dd, J=15.3, 6.0 Hz, 1H), 4.35; (dd, J=15.3, 5.4 Hz, 1H), 4.14; (br-s, 2H), 3.85; (br-s, 1H), 3.13; (dd, J=12.7, 6.5 Hz, 2H), 3.00; (br-s, 2H), 2.05-1.92; (m, 4H), 1.90-1.80; (m, 2H), 1.78-1.70; (m, 2H), 1.60; (d, J=12.2 Hz, 1H), 1.54-

1.46; (m, 1H), 1.30-1.17; (m, 4H), 1.13-1.05; (m, 1H). HRMS (ESI, m/z): [M+H]$^+$598.4236.

Example 17: Preparation of Compound 12

The synthetic processes and conditions for the preparation of compound 12 were similar to that of compound 1.
$^1$H NMR (400 MHz, DMSO-d$_6$) (δ 9.64; (br-s, 1H), 9.24; (br-s, 3H), 8.69; (br-s, 2H), 8.21; (br-s, 2H), 8.20; (s, 1H), 8.02; (s, 1H), 7.66-7.09; (m, 8H), 4.46-4.27; (m, 4H), 4.14; (br-s, 2H), 3.93; (br-s, 1H), 3.14; (dd, J=12.2, 6.1 Hz, 2H), 3.00; (br-s, 5H), 1.97-1.74; (m, 8H), 1.60; (d, J=12.1 Hz, 1H), 1.56-1.45; (m, 2H), 1.32-1.17; (m, 4H), 1.16-1.03; (m, 1H). HRMS (ESI, m/z): [M+H]+658.3674.

Example 18: Preparation of Compound 13

The synthetic processes and conditions for the preparation of compound 13 were similar to that of compound 1.
$^1$H NMR (400 MHz, DMSO-d$_6$) (δ 9.26; (br-s, 2H), 8.94; (s, 1H), 8.74; (br-s, 2H), 7.94; (d, J=5.3 Hz, 1H), 7.83-6.87; (m, 11H), 4.35; (d, J=3.7 Hz, 2H), 4.20; (br-s, 2H), 4.13; (br-s, 2H), 3.57; (br-s, 1H), 3.10; (d, J=6.1 Hz, 2H), 3.00; (br-s, 5H), 1.98; (br-s, 4H), 1.76-1.68; (m, 4H), 1.61-1.50; (m, 3H), 1.29-1.18; (m, 4H), 1.13-1.05; (m, 1H). HRMS (ESI, m/z): [M+H]$^+$512.3829.

Example 19: Preparation of Compound 14

The synthetic processes and conditions for the preparation of compound 14 were similar to that of compound 1.
$^1$H NMR (400 MHz, D$_2$O) (δ 8.52; (d, J=5.3 Hz, 1H), 8.08; (d, J=7.8 Hz, 1H), 7.72-7.66; (m, 1H), 7.40; (d, J=8.0 Hz, 2H), 7.35; (d, J=8.0 Hz, 2H), 4.61; (t, J=4.9 Hz, 1H), 4.39; (s, 2H), 4.25; (dd, J=8.2, 5.1 Hz, 1H), 4.19; (s, 2H), 3.17-3.00; (m, 7H), 2.98-2.82; (m, 2H), 2.14-1.85; (m, 9H), 1.82-1.71; (m, 3H), 1.64-1.46; (m, 3H), 1.31-1.18; (m, 4H), 1.15-1.05; (m, 1H). HRMS (ESI, m/z): [M+H]$^+$563.4183.

Example 20: Preparation of Compound 15

The synthetic processes and conditions for the preparation of compound 15 were similar to that of compound 1.
$^1$H NMR (400 MHz, DMSO-d$_6$) (δ 9.36; (t, J=5.8 Hz, 1H), 9.29; (br-s, 2H), 9.03-8.85; (m, 2H), 8.75; (br-s, 2H), 8.05; (t, J=5.6 Hz, 1H), 7.64-7.16; (m, 8H), 4.53; (dd, J=15.4, 6.4 Hz, 1H), 4.29; (dd, J=15.3, 5.0 Hz, 1H), 4.14; (br-s, 2H), 3.96; (br-s, 1H), 3.14; (dd, J=13.3, 7.0 Hz, 2H), 3.00; (br-s, 5H), 2.79; (br-s, 1H), 2.12-1.86; (m, 6H), 1.83-1.67; (m, 6H), 1.64-1.55; (m, 2H), 1.54-1.44; (m, 2H), 1.32-1.01; (m, 10H). HRMS (ESI, m/z): [M+H]$^+$514.4226.

Example 21: Preparation of Compound 16

The synthetic processes and conditions for the preparation of compound 16 were similar to that of compound 1.
$^1$H NMR (400 MHz, D$_2$O) (δ 7.43; (d, J=7.8 Hz, 1H), 7.38; (d, J=7.8 Hz, 1H), 4.44; (q, J=15.1 Hz, 2H), 4.21; (br-s, 2H), 3.84; (br-s, 1H), 3.20-2.97; (m, 7H), 2.87-2.82; (m, 1H), 2.68-2.63; (m, 1H), 2.09-2.00; (m, 4H), 1.94-1.86; (m, 2H), 1.79; (br-s, 2H), 1.70-1.40; (m, 9H), 1.35-1.05; (m, 8H), 0.99-0.82; (m, 2H). HRMS (ESI, m/z): [M+H]$^+$ 528.4393.

Example 22: Preparation of Compound 17

Referring to the synthesis scheme (3), except that Fmoc-Lys(Boc)-OH was used as the amino acid raw material, the remaining synthetic processes and conditions for the preparation of compound 17 were similar to that of compound 1.
$^1$H NMR (400 MHz, D$_2$O) (δ 8.62; (br-s, 1H), 8.08; (t, J=6.8 Hz, 1H), 7.63 (br-s, 2H), 7.45; (d, J=6.5 Hz, 2H), 7.38; (d, J=6.5 Hz, 2H), 4.50-4.30; (m, 4H), 4.24; (br-s, 2H), 3.99; (br-s, 1H), 3.25-3.00; (m, 5H), 2.99-2.85; (m, 2H), 2.15-1.89; (m, 6H), 1.88-1.74; (m, 2H), 1.73-1.56; (m, 3H), 1.47-1.21; (m, 6H), 1.20-1.08; (m, 1H). HRMS (ESI, m/z): [M+H]$^+$495.3810.

Example 23: Preparation of Compound 18

Referring to the synthesis scheme (3), except that the synthesized intermediate 2-3a was used as the amino acid raw material, the remaining synthetic processes and conditions for the preparation of compound 18 were similar to that of compound 1.
$^1$H NMR (400 MHz, D$_2$O) (δ 8.76; (d, J=5.3 Hz, 1H), 8.47; (td, J=7.9, 1.1 Hz, 1H), 8.03; (d, J=8.0 Hz, 1H), 8.01-7.92; (m, 1H), 7.43; (d, J=8.1 Hz, 2H), 7.35; (d, J=8.1 Hz, 2H), 4.64; (d, J=14.3 Hz, 1H), 4.51; (d, J=14.3 Hz, 1H), 4.46-4.32; (m, 2H), 4.21; (br-s, 2H), 4.12; (t, J=6.4 Hz, 1H), 3.34-3.28; (m, 1H), 3.15-3.03; (m, 5H), 2.98-2.84; (m, 2H), 2.09-1.93; (m, 6H), 1.77; (br-s, 1H), 1.69-1.54; (m, 3H), 1.42-1.31; (m, 2H), 1.30-1.18; (m, 10H), 1.17-1.07; (m, 1H). HRMS (ESI, m/z): [M+H]$^+$537.4280.

Example 24: Preparation of Compound 19

Referring to the synthesis scheme (3), except that the synthesized intermediate 2-3b was used as the amino acid raw material, the remaining synthetic processes and conditions for the preparation of compound 19 were similar to that of compound 1.
$^1$H NMR (400 MHz, D$_2$O) δ 8.70; (d, J=5.0 Hz, 1H), 8.34; (t, J=7.8 Hz, 1H), 7.92-7.83; (m, 2H), 7.40; (d, J=8.0 Hz, 2H), 7.33; (d, J=8.0 Hz, 2H), 4.57-4.42; (m, 2H), 4.37; (s, 2H), 4.19; (s, 2H), 4.05; (t, J=6.3 Hz, 1H), 3.12-2.94; (m, 6H), 2.92-2.88; (m, 2H), 2.05-1.90; (m, 8H), 1.82-1.68; (m, 4H), 1.65-1.53; (m, 4H), 1.35-1.15; (m, 10H), 1.12-1.05; (m, 2H). HRMS (ESI, m/z): [M+H]$^+$577.4584.

Example 25: Preparation of Compound 20

Referring to the synthesis scheme (3), except that the synthesized intermediate 2-3c was used as the amino acid raw material, the remaining synthetic processes and conditions for the preparation of compound 20 were similar to that of compound 1.
$^1$H NMR (400 MHz, D$_2$O) δ 8.59; (d, J=5.6 Hz, 1H), 8.36; (td, J=8.0, 1.3 Hz, 1H), 7.94; (d, J=8.0 Hz, 1H), 7.87-7.81; (m, 1H), 7.22; (d, J=8.1 Hz, 2H), 7.14; (d, J=8.1 Hz, 2H), 4.51 (d, J=14.3 Hz, 1H), 4.35; (d, J=14.3 Hz, 1H), 4.20; (s, 2H), 4.00; (s, 3H), 2.96-2.75; (m, 8H), 1.89-1.75; (m, 8H), 1.56-1.48; (m, 6H), 1.38; (d, J=12.2 Hz, 2H), 1.11-0.99; (m, 8H), 0.95-0.85; (m, 2H). HRMS (ESI, m/z): [M+H]$^+$ 563.4428.

Example 26: Preparation of Compound 21

Referring to the synthesis scheme (3), except that Fmoc-His(Trt)-OH was used as the amino acid raw material, the remaining synthetic processes and conditions for the preparation of compound 21 were similar to that of compound 1.
$^1$H NMR (400 MHz, D$_2$O) δ 8.66; (d, J=5.6 Hz, 1H), 8.43; (t, J=7.9 Hz, 1H), 8.33; (s, 1H), 7.99; (d, J=8.0 Hz, 1H), 7.95-7.86; (m, 1H), 7.25; (d, J=7.9 Hz, 2H), 7.13-6.96; (m, 3H), 4.57; (d, J=14.5 Hz, 1H), 4.44; (d, J=14.5 Hz, 1H), 4.25; (d, J=14.8 Hz, 1H), 4.19; (dd, J=9.3, 5.5 Hz, 1H), 4.08; (s, 2H), 4.04; (d, J=14.9 Hz, 1H), 3.32; (dd, J=15.0, 5.3 Hz, 1H), 3.18; (dd, J=15.0, 9.4 Hz, 1H), 3.01-2.90; (m, 5H), 1.99-1.79; (m, 4H), 1.63; (br-s, 2H), 1.45; (d, J=12.3 Hz, 1H), 1.23-1.02; (m, 4H), 1.00-0.92; (m, 1H). HRMS (ESI, m/z): [M+H]$^+$504.3451.

Example 27: Preparation of Compound 22

Referring to the synthesis scheme (3), except that Fmoc-Asp(tBu)-OH was used as the amino acid raw material, the remaining synthetic processes and conditions for the preparation of compound 22 were similar to that of compound 1.
$^1$H NMR (400 MHz, D$_2$O) δ 8.49; (d, J=5.0 Hz, 1H), 8.05; (t, J=7.4 Hz, 1H), 7.60-7.54; (m, 2H), 7.30; (d, J=7.9 Hz, 2H), 7.21; (d, J=7.9 Hz, 2H), 4.35-4.18; (m, 4H), 4.10; (br-s, 2H), 4.01; (t, J=6.2 Hz, 1H), 3.05-2.93; (m, 5H), 2.85; (d, J=6.1 Hz, 2H), 1.96-1.84; (m, 4H), 1.68; (br-s, 2H), 1.50; (d, J=12.2 Hz, 1H), 1.21-1.09; (m, 4H), 1.05-0.95; (m, 1H). HRMS (ESI, m/z): [M+H]$^+$482.3127.

Example 28: Preparation of Compound 23

Referring to the synthesis scheme (3), except that Fmoc-Ala-OH was used as the amino acid raw material, the remaining synthetic processes and conditions for the preparation of compound 23 were similar to that of compound 1.
$^1$H NMR (400 MHz, D$_2$O) δ 8.72; (d, J=5.7 Hz, 1H), 8.50; (t, J=7.9 Hz, 1H), 8.07; (d, J=8.0 Hz, 1H), 8.01-7.93; (m, 1H), 7.32; (d, J=8.0 Hz, 2H), 7.24; (d, J=8.0 Hz, 2H), 4.63 (d, J=14.4 Hz, 1H), 4.51; (d, J=14.3 Hz, 1H), 4.30; (dd, J=33.3, 15.4 Hz, 2H), 4.18; (q, J=7.0 Hz, 1H), 4.11; (s, 2H), 3.06-2.90; (m, 5H), 2.03-1.85; (m, 4H), 1.67; (d, J=6.0 Hz, 2H), 1.54-1.45; (m, 4H), 1.23-1.11; (m, 4H), 1.08-0.95; (m, 1H). HRMS (ESI, m/z): [M+H]$^+$438.3235.

Example 29: Preparation of Compound 24

Referring to the synthesis scheme (3), except that Fmoc-Ser(tBu)-OH was used as the amino acid raw material, the remaining synthetic processes and conditions for the preparation of compound 24 were similar to that of compound 1.
$^1$H NMR (400 MHz, D$_2$O) δ 8.53; (d, J=5.0 Hz, 1H), 8.04; (t, J=7.6 Hz, 1H), 7.63; (d, J=7.8 Hz, 1H), 7.61-7.52; (m, 1H), 7.35; (d, J=7.7 Hz, 2H), 7.26; (d, J=7.7 Hz, 2H), 4.43-4.25; (m, 4H), 4.15; (s, 2H), 4.08-3.95; (m, 2H), 3.92-3.85; (m, 1H), 3.11-2.90; (m, 5H), 2.05-1.86; (m, 4H), 1.72; (br-s, 2H), 1.54; (d, J=12.2 Hz, 1H), 1.25-1.13; (m, 4H), 1.09-1.03; (s, 1H). HRMS (ESI, m/z): [M+H]$^+$ 454.3179.

Example 30: Preparation of Compound 25

Referring to the synthesis scheme (3), except that Fmoc-2-Nal-OH was used as the amino acid raw material, the remaining synthetic processes and conditions for the preparation of compound 25 were similar to that of compound 1.
$^1$H NMR (400 MHz, D$_2$O) δ 8.66; (d, J=5.1 Hz, 1H), 8.18; (td, J=7.8, 1.3 Hz, 1H), 7.86; (d, J=7.8 Hz, 1H), 7.77-7.69; (m, 4H), 7.56-7.49; (m, 3H), 7.27 (d, J=8.4 Hz, 1H), 6.84; (d, J=8.0 Hz, 2H), 6.63; (d, J=8.0 Hz, 2H), 4.49; (q, J=14.4 Hz, 2H), 4.31-4.26; (m, 2H), 4.01; (q, J=13.1 Hz, 2H), 3.86; (d, J=15.0 Hz, 1H), 3.52; (dd, J=13.1, 5.2 Hz, 1H), 3.24-3.13; (m, 1H), 3.06-3.01; (m, 5H), 2.09-1.89; (m, 4H), 1.79; (br-s, 2H), 1.62; (d, J=12.0 Hz, 1H), 1.36-1.19; (m, 5H), 1.13-1.08; (m, 1H). HRMS (ESI, m/z): [M+H]$^+$564.3712.

Example 31: Preparation of Compound 26

Referring to the synthesis scheme (3), except that Fmoc-Trp(Boc)-OH was used as the amino acid raw material, the remaining synthetic processes and conditions for the preparation of compound 26 were similar to that of compound 1.
$^1$H NMR (400 MHz, D$_2$O) δ 8.73; (d, J=5.5 Hz, 1H), 8.43; (t, J=7.9 Hz, 1H), 7.98; (d, J=8.0 Hz, 1H), 7.95-7.89; (m, 1H), 7.48; (dd, J=7.8, 4.4 Hz, 2H), 7.26-7.20; (m, 3H), 7.14; (s, 1H), 7.08; (t, J=7.5 Hz, 1H), 6.82; (d, J=7.8 Hz, 2H), 4.61; (dd, J=34.7, 14.4 Hz, 2H), 4.33; (dd, J=9.5, 5.7 Hz, 1H), 4.26; (d, J=15.2 Hz, 1H), 4.19; (s, 2H), 4.02; (d, J=15.1 Hz, 1H), 3.50-3.45; (m, 1H), 3.40-3.34; (m, 1H), 3.14-3.00; (m, 5H), 2.08-1.98; (m, 4H), 1.79 (br-s, 2H), 1.62; (d, J=12.0 Hz, 1H), 1.32-1.21; (m, 4H), 1.17-1.10; (s, 1H). HRMS (ESI, m/z): [M+H]$^+$553.3651.

Example 32: Preparation of Compound 27

Referring to the synthesis scheme (3), except that Fmoc-Tyr(tBu)-OH was used as the amino acid raw material, the remaining synthetic processes and conditions for the preparation of compound 27 were similar to that of compound 1.
$^1$H NMR (400 MHz, D$_2$O) δ 8.50; (d, J=4.1 Hz, 1H), 7.92; (t, J=7.5 Hz, 1H), 7.47; (t, J=7.0 Hz, 2H), 7.22; (d, J=7.6 Hz, 2H), 6.86; (t, J=9.2 Hz, 4H), 6.58; (d, J=8.0 Hz, 2H), 4.32-4.23; (m, 3H), 4.12; (s, 2H), 3.98-3.87; (m, 2H), 3.18-3.13; (m, 1H), 3.08-2.92; (m, 5H), 2.90-2.80; (m, 1H), 2.05-1.82; (m, 4H), 1.69; (br-s, 2H), 1.52; (d, J=12.1 Hz, 1H), 1.25-1.10; (m, 4H), 1.08-0.99; (m, 1H). HRMS (ESI, m/z): [M+H]$^+$530.3500.

Example 33: Preparation of Compound 28

Referring to the synthesis scheme (3), except that Fmoc-Leu-OH was used as the amino acid raw material, the remaining synthetic processes and conditions for the preparation of compound 28 were similar to that of compound 1.
$^1$H NMR (400 MHz, D$_2$O) δ 8.48; (d, J=4.7 Hz, 1H), 7.86; (t, J=7.5 Hz, 1H), 7.45-7.38; (m, 2H), 7.31; (d, J=7.9 Hz, 2H), 7.24; (d, J=7.9 Hz, 2H), 4.34; (d, J=15.1 Hz, 1H), 4.25-4.15; (m, 3H), 4.11; (s, 2H), 3.81; (dd, J=8.7, 5.8 Hz, 1H), 3.05-2.90; (m, 5H), 1.98-1.85; (m, 4H), 1.73-1.55; (m, 4H), 1.51; (d, J=12.1 Hz, 1H), 1.42-1.35; (m, 1H), 1.23-1.10; (m, 4H), 1.06-0.95; (m, 1H), 0.76; (d, J=6.4 Hz, 3H), 0.72; (d, J=6.5 Hz, 3H). HRMS (ESI, m/z): [M+H]$^+$ 480.3702.

Example 34: Preparation of Compound 29

Referring to the synthesis scheme (3), except that Fmoc-Pro-OH was used as the amino acid raw material, the remaining synthetic processes and conditions for the preparation of compound 29 were similar to that of compound 1.
$^1$H NMR (400 MHz, D$_2$O) δ 8.45; (d, J=4.7 Hz, 1H), 7.95; (t, J=7.6 Hz, 1H), 7.64; (d, J=7.8 Hz, 1H), 7.56-7.46; (m, 1H), 7.39; (d, J=7.8 Hz, 2H), 7.19; (d, J=7.8 Hz, 2H), 4.67; (d, J=13.6 Hz, 1H), 4.46; (d, J=13.6 Hz, 1H), 4.40-4.29; (m, 1H), 4.21; (s, 2H), 4.19; (s, 2H), 3.85-3.76; (m, 1H), 3.43-3.36; (m, 1H), 3.17-3.00; (m, 5H), 2.62-2.49; (m, 1H), 2.27-2.13; (m, 1H), 2.09-1.92; (m, 6H), 1.77; (br-s, 2H), 1.59 (d, J=12.2 Hz, 1H), 1.32-1.17; (m, 4H), 1.15-1.05; (m, 1H). HRMS (ESI, m/z): [M+H]$^+$464.3395.

Example 35: Preparation of Compound 30

Referring to the synthesis scheme (3), except that Fmoc-L-1,2,3,4-tetrahydroxyisoquinoline-3-carboxylic acid was used as the amino acid raw material, the remaining synthetic processes and conditions for the preparation of compound 30 were similar to that of compound 1.
$^1$H NMR (400 MHz, D$_2$O) δ 8.58; (d, J=5.2 Hz, 1H), 8.19; (td, J=7.9, 1.4 Hz, 1H), 7.75; (d, J=7.9 Hz, 1H), 7.73-7.65; (m, 1H), 7.41; (d, J=8.1 Hz, 1H), 7.35-7.20; (m, 5H), 7.18-7.10; (m, 2H), 4.64-4.34; (m, 3H), 4.33-4.12; (m, 5H), 3.37-3.30; (m, 1H), 3.26-3.16; (m, 1H), 3.15-3.05; (m, 5H), 2.12-1.91; (m, 4H), 1.78; (br-s, 2H), 1.61; (d, J=12.1 Hz, 1H), 1.39-1.17; (m, 4H), 1.19-1.01; (m, 1H). HRMS (ESI, m/z): [M+H]$^+$526.3555.

Example 36: Preparation of Compound 31

Referring to the synthesis scheme (3), the intermediate 1-3a (3.20 g) was condensed with a first amino acid raw material Fmoc-Arg(Pbf)-OH to obtain an intermediate, which was deprotected to remove the Fmoc protective group and then condensed with a second amino acid raw material Fmoc-Tyr(tBu)-OH, followed by removal of Fmoc, Pbf, tBu and Boc protective groups. The synthetic conditions were similar to that of compound 2.

$^1$H NMR (400 MHz, CD$_3$OD) δ 7.46; (d, J=8.0 Hz, 2H), 7.38; (d, J=7.9 Hz, 2H), 7.24; (d, J=2.0 Hz, 1H), 7.10-7.01; (m, 1H), 6.85; (d, J=8.3 Hz, 1H), 6.72; (d, J=8.5 Hz, 1H), 4.53-4.30; (m, 3H), 4.20; (s, 2H), 4.15-4.55; (m, 1H), 3.26-3.00; (m, 8H), 2.98-2.90; (m, 1H), 2.18-2.03; (m, 4H), 1.95-1.80; (m, 3H), 1.80-1.56; (m, 4H), 1.41-1.28; (m, 4H), 1.25-1.17; (m, 1H). HRMS (ESI, m/z): [M+H]$^+$595.4086.

Example 37: Preparation of Compound 32

Referring to the synthesis scheme (3), the intermediate 1-3a (3.20 g) was condensed with a first amino acid raw material Fmoc-2-Nal-OH to obtain an intermediate, which was deprotected to remove the Fmoc protective group and then condensed with a second amino acid raw material Fmoc-Arg(Pbf)-OH, followed by removal of Fmoc, Pbf, tBu and Boc protective groups. The synthetic conditions were similar to that of compound 2.

$^1$H NMR (400 MHz, D$_2$O) δ 7.87; (d, J=7.2 Hz, 1H), 7.79; (d, J=8.5 Hz, 1H), 7.77-7.71; (m, 1H), 7.59; (s, 1H), 7.56-7.47; (m, 2H), 7.36; (d, J=8.5 Hz, 1H), 6.86; (d, J=8.1 Hz, 2H), 6.69; (d, J=8.0 Hz, 2H), 4.68; (dd, J=10.3, 6.3 Hz, 1H), 4.33; (d, J=15.3 Hz, 1H), 4.08-3.97; (m, 3H), 3.94; (d, J=15.3 Hz, 1H), 3.31; (dd, J=13.3, 6.2 Hz, 1H), 3.15-2.98; (m, 8H), 2.06-1.93; (m, 4H), 1.92-1.84; (m, 2H), 1.82-1.72; (m, 2H), 1.66-1.49; (m, 3H), 1.33-1.18; (m, 4H), 1.17-1.04; (m, 1H). HRMS (ESI, m/z): [M+H]$^+$629.4282.

Example 38 Cytotoxicity Assay of Compounds

1. Experimental method: the experiment was carried out using HEK293 cell line. The HEK293 cells cultured in DMEM medium (containing 10% fetal bovine serum, 100 IU penicillin and 0.1 mg/ml streptomycin) were trypsinized, counted, and plated in a 96-well plate with each well containing 100 μl suspension and including 3×10$^3$ cells in total. After culturation in a constant-temperature incubator containing 5% CO$_2$ at 37° C. overnight, different concentrations of the compound were added. After 72 hours of incubation in total, 20 μl CellTiter 96 was added to further incubate for 1 to 4 hours, and then an absorption value at 490 nm was measured on a microplate reader. The changes in cell viability prior to and subsequent to the addition of the compound were observed by comparing the values of the blank control group and the experimental group.

2. Experimental results: as shown in Table 1, the compounds have no cytotoxic effect and do not have inhibitory activity on cytogenesis at a concentration of 50 μM.

Example 39 Binding Affinity Assay of Compounds on CXCR4 Receptor Protein

3. Experimental method: the cell line used for the affinity activity assay of the CXCR4 was a CHO cell line constructed in vitro and stably transfected with CXCR4. The CHO cell line cultured in DMEM medium (containing 10% fetal bovine serum, 100 IU penicillin, 0.1 mg/ml streptomycin and 0.2 mg/ml G418) was trypsinized, washed, counted, and then suspended in an FACS buffer (PBS containing 0.5% BSA and 0.05% NaN$_3$), followed by being plated in a 96-well plate. Each cell contains 100 μl of the reaction system, which includes 5×10$^5$ cells, 250 ng/ml 12G5 monoclonal antibody and different concentrations of compound for detection. After incubated on ice for 40 min and washed with the FACS buffer, the reaction system was added with the secondary antibody (anti-mouse FITC-labeled IgG) for further incubation on ice for 30 min and then washed twice with the FACS buffer. Absorption values at 485 nmEX/535 nmEM were measured on a microplate reader (PerkinElmer), and fluorescence intensities were recorded. For each compound, a percentage of the compound that inhibits the binding of the 12G5 monoclonal antibody to the receptor CXCR4, i.e. a binding inhibition ratio at 0.1 μM, was calculated.

4. Experimental results: as shown in Table 1, most of the compounds show a strong inhibitory activity at the concentration of 0.1 μM. The inhibition ratio of the compounds is divided into the following intervals: 75% to 100% for A, 50% to 74% for B, 25% to 49% for C, and 0 to 24% for D.

TABLE 1

| Compound No. | Chemical structural formula | Inhibition ratio interval of compounds at 0.1 μM | Cytotoxicity assay (IC$_{50}$, μM) |
|---|---|---|---|
| 1 | (structure) | A | >50 |

TABLE 1-continued

| Compound No. | Chemical structural formula | Inhibition ratio interval of compounds at 0.1 μM | Cytotoxicity assay (IC$_{50}$, μM) |
|---|---|---|---|
| 2 | | B | >50 |
| 3 | | D | NT |
| 4 | | D | >50 |
| 5 | | C | >50 |
| 6 | | B | >50 |

TABLE 1-continued

| Compound No. | Chemical structural formula | Inhibition ratio interval of compounds at 0.1 μM | Cytotoxicity assay (IC$_{50}$, μM) |
| --- | --- | --- | --- |
| 7 | | B | >50 |
| 8 | | B | >50 |
| 9 | | A | >50 |
| 10 | | B | >50 |

TABLE 1-continued

| Compound No. | Chemical structural formula | Inhibition ratio interval of compounds at 0.1 μM | Cytotoxicity assay (IC$_{50}$, μM) |
|---|---|---|---|
| 11 | | B | >50 |
| 12 | | D | >50 |
| 13 | | B | >50 |
| 14 | | D | NT |
| 15 | | B | >20 |

TABLE 1-continued

| Compound No. | Chemical structural formula | Inhibition ratio interval of compounds at 0.1 μM | Cytotoxicity assay (IC$_{50}$, μM) |
|---|---|---|---|
| 16 | | A | >50 |
| 17 | | A | >50 |
| 18 | | A | >50 |
| 19 | | A | >50 |
| 20 | | B | >50 |

TABLE 1-continued

| Compound No. | Chemical structural formula | Inhibition ratio interval of compounds at 0.1 μM | Cytotoxicity assay (IC$_{50}$, μM) |
|---|---|---|---|
| 21 | | A | >50 |
| 22 | | B | >50 |
| 23 | | A | >50 |
| 24 | | A | >50 |
| 25 | | B | >10 |

TABLE 1-continued

| Compound No. | Chemical structural formula | Inhibition ratio interval of compounds at 0.1 μM | Cytotoxicity assay (IC$_{50}$, μM) |
|---|---|---|---|
| 26 | | A | >50 |
| 27 | | B | >50 |
| 28 | | C | >50 |
| 29 | | A | >50 |
| 30 | | A | >20 |

TABLE 1-continued

| Compound No. | Chemical structural formula | Inhibition ratio interval of compounds at 0.1 µM | Cytotoxicity assay (IC$_{50}$, µM) |
|---|---|---|---|
| 31 | 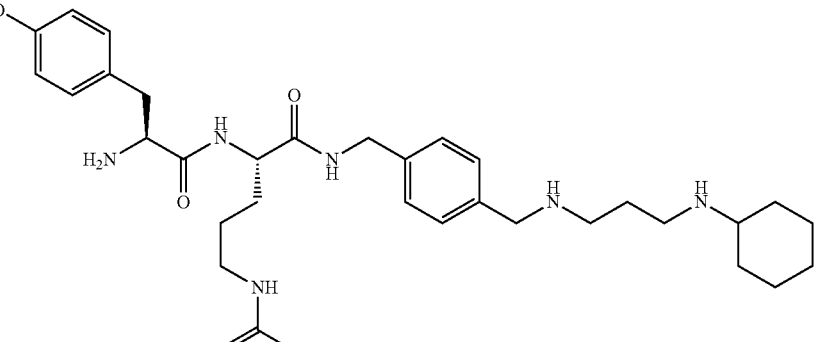 | A | >50 |
| 32 | 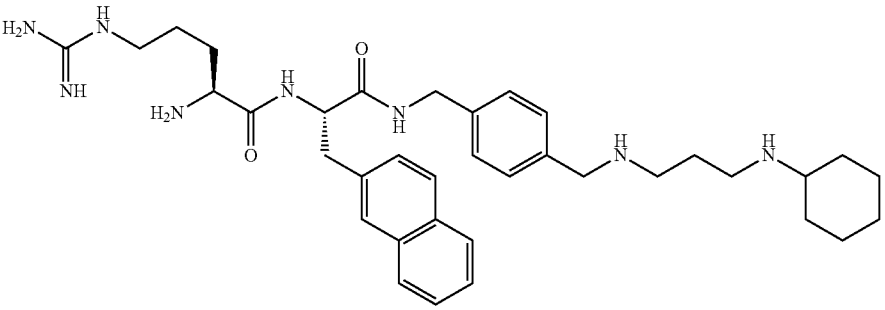 [SMILES: N=C(N)NCCC[C@H](N)C(=O)N[C@@H](Cc1ccc2ccccc2c1)C(=O)NCc1ccc(CNCCCNC2CCCCC2)cc1] | A | >50 |

Note:
"–" indicates no inhibitory activity, and "NT" indicates without detection.

Example 40 Assay on the Inhibition of Compounds on CXCR4 Induced Cell Migration

1. Experimental method: the assay on the CXCR4 induced cell migration was detected using SupT1 cell line which naturally expresses the CXCR4. SupT1 cells cultured and suspended in RPMI 1640 (containing 10% fetal bovine serum, 100 IU penicillin and 0.1 mg/ml streptomycin) were collected and then washed with RPMI 1640 containing 0.5% BSA, after which the cells are counted and suspended to a concentration of $3.0 \times 10^7$ cells/ml, and then uniformly mixed with different concentrations of compound. Then, 75 µl of the obtained mixture was taken and added to a tranwell insert, and incubated at 37° C. for 30 min. Subsequently, 200 µl of RPMI 1640 containing 0.5% BSA of 2 nM SDF-1α was added to each well of a lower culture plate, and a group to be used as a background value did not contain SDF-1α. After incubation at 37° C. for 3 hours, the tranwell insert was removed, and 40 µl of CellTiter 96 (Promega) was added to each cell of the lower culture plate. After 1 to 4 hours of incubation, absorption values at 490 nm were detected. The experimental results of each group were obtained by at least three independent experiments, and the inhibition curve was plotted by the GraphPad software.
2. Experimental results: as shown in FIG. 1, in the CXCR4 induced cell migration inhibiting experiments, the exemplified compound 1 has a significant inhibiting ability to the cell migration, which exhibits a good concentration-dependent relationship, indicating that the compounds according to embodiments of the present disclosure have a significant inhibiting ability to the cell migration, and such inhibiting ability is concentration-dependent.

Figure 2:
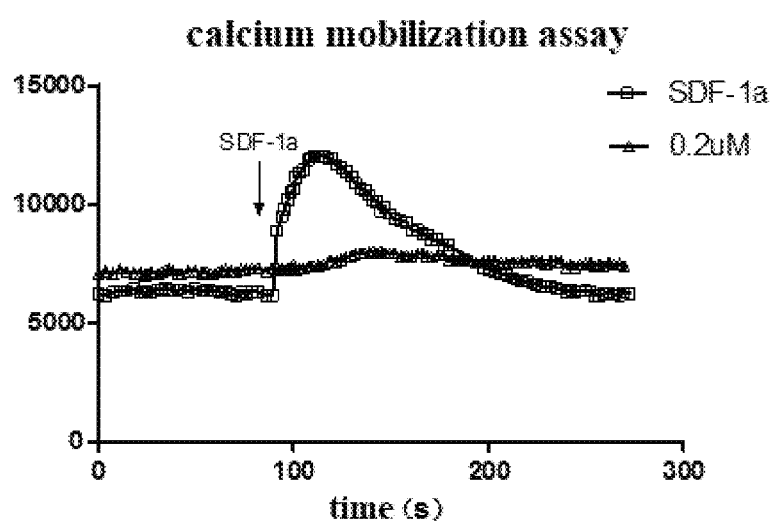
FIG. 2 is a graph showing experimental results of an activity of compound 1 to inhibit intracellular calcium mobilization according to an embodiment of the present disclosure.
Figure 3:
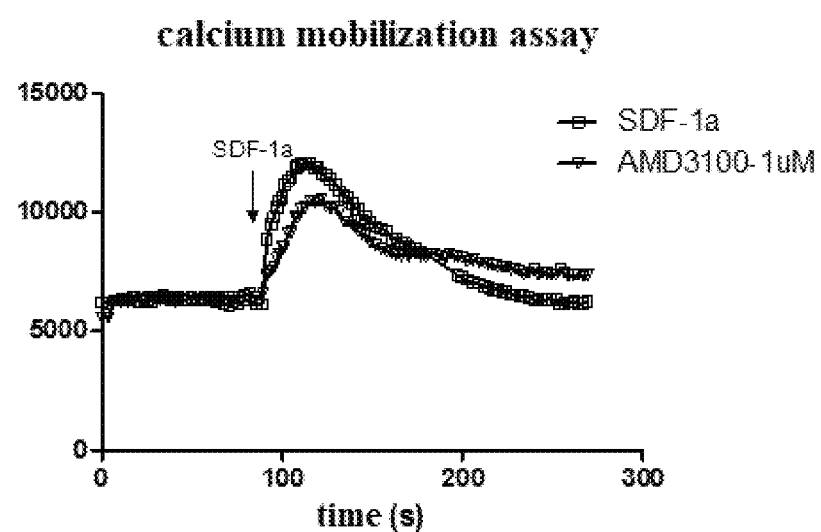
FIG. 3 is a graph showing experimental results of an activity of a positive agent AMD3100 to inhibit intracellular calcium mobilization according to an embodiment of the present disclosure.

Example 41 Assay on the Inhibition of Compounds on Intracellular Calcium Mobilization 3. Experimental method: the cell line used in this assay was SupT1. Prior to the experiment, the cells were collected and washed with an experimental buffer (an HBSS buffer containing 20 mM HEPES), and then incubated with a buffer containing 4 µM Fluo-4 and 1 mM probenecid sodium for 30 min at 37° C., after which the residual dye was washed away, and the cells were suspended to a concentration of $2 \times 10^6$ cells/ml. Afterwards, 200 µl of the cell suspension was taken and added to a black 96-well plate, and absorption values of the cells at 494 nmEX/516 nmEM were recorded. Subsequently, different concentrations of compound were added and mixed uniformly, and the baseline was recorded. Thereafter, 50 nM of the SDF-1α was added and mixed uniformly. Signals of calcium ions were recorded, and the differences in fluorescence intensity between a group without addition of the compound and groups added with different concentrations of the compound were observed.
4. Experimental results: as shown in FIG. 2, the exemplified compound 1 can completely inhibit the generation of signal of the calcium mobilization at a concentration of 0.2 µM, while the positive agent AMD3100 fails to inhibit the signal of the calcium mobilization at a concentration of 1.0 µM (as shown in FIG. 3). As can be seen from the results of the exemplified compound 1, the CXCR4 antagonistic activity exhibited by the compound according to embodiments of the present disclosure is superior to that of AMD3100.

Reference throughout this specification to "an embodiment," "some embodiments," "one embodiment", "an example," "a specific example," or "some examples," means that a particular feature, structure, material, or characteristic described in connection with the embodiment or example is included in at least one embodiment or example of the present disclosure. Thus, the appearances of the phrases such as "in an embodiment," "in some embodiment", "in one embodiment", "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, in the absence of contradiction, different embodiments or examples of the present disclosure or features described in different embodiments or examples may be combined by those skilled in the art.

Although embodiments of the present disclosure have been shown and described above, it would be appreciated by those skilled in the art that the above embodiments are exemplary, cannot be construed to limit the present disclosure, and changes, modifications, alternatives and variants can be made in the embodiments without departing from the scope of the present disclosure.

What is claimed is:

1. A compound of formula (I), or a pharmaceutically acceptable salt or prodrug thereof:

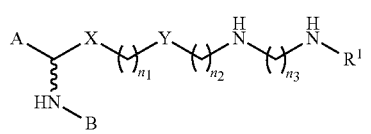

wherein $n_1$ and $n_2$ are each 1 or 2, $n_3$ is 3 or 4;
$R^1$ represents cyclohexyl;
X represents —C(=O)NR$^2$, wherein R$^2$ represents hydrogen, or methyl;
Y represents benzene or pyridine connected at para-positions;

wherein  is

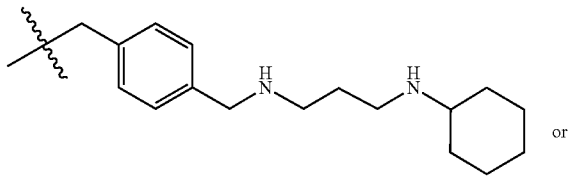 or

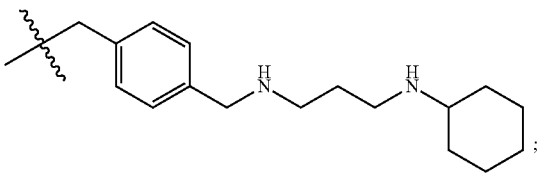;

A represents methyl,

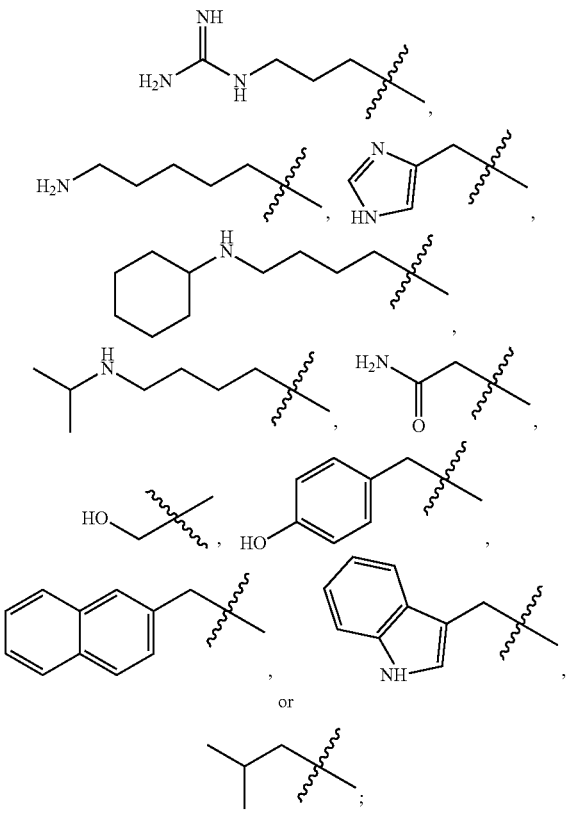

or

A can form a monocyclic or bicyclic ring together with HN⟶;
B represents hydrogen, alkyl, cycloalkyl, aryl, heteroaryl, an amino acid substituent, or a group of formula (v) or (vi):

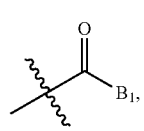

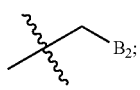

wherein $B_1$ and $B_2$ are each independently an optionally substituted cycloalkyl, aryl or heteroaryl;
wherein
(1) when B is the cycloalkyl, B is cyclopentyl, cyclohexyl, mono- or poly-substituted cyclohexyl methyl, pyridine-fused cyclohexyl;
(2) when B is the aryl, B is phenyl, biphenyl, or naphthyl;
(3) when B is the heteroaryl, B is imidazolyl, unsubstituted pyridyl, mono- or poly-substituted pyridyl;
(4) when B is the amino acid substituent, B is an L- or D-α-amino acid;
(5) when B is aryl-, heteroaryl-, saturated carbocyclic or heterocyclic ring-substituted alkyl or formyl, B is

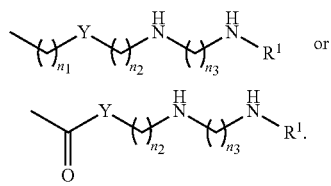

2. The compound according to claim 1, wherein

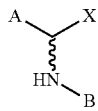

is an amino acid, and the amino acid is a natural or non-natural amino acid, wherein the amino acid is an α-amino acid, a β-amino acid, or a γ-amino acid, wherein a side chain of the α-amino acid is cyclized or not cyclized with an —NH$_2$ terminal, and the amino acid comprises an L- or D-amino acid, wherein the α-amino acid comprises at least one selected from a group comprising arginine, lysine, citrulline, ornithine, histidine, aspartic acid, glutamic acid, glutamine, asparagine, serine, threonine, cysteine, phenylalanine, 3-(2-naphthyl) alanine, cyclohexylalanine, tryptophan, 5-hydroxytryptophan, tyrosine, glycine, phenylglycine, cyclohexylglycine, alanine, valine, leucine, isoleucine, methionine, proline, 4-hydroxyproline, 1-amino-1-cyclohexanecarboxylic acid and 1,2,3,4-tetrahydroisoquinolyl-3-carboxylic acid.

3. The compound according to claim 1, wherein A forms a monocyclic ring together with HN~, and the compound of formula (I) has the following structures:

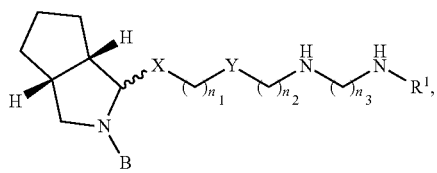

4. The compound according to claim 1, wherein A forms a bicyclic ring together with HN~, and the compound of formula (I) has the following structures:

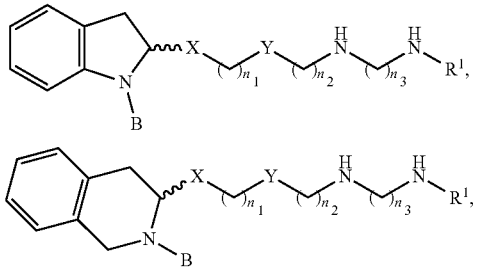

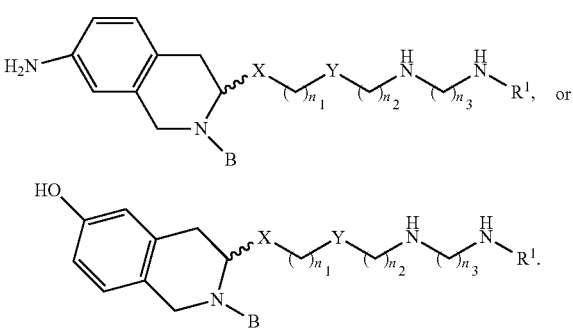

5. The compound according to claim 1, wherein the pharmaceutically acceptable salt comprises at least one selected from a group comprising trifluoroacetate, hydrochloride, acetate, sulfate, mesylate, tosylate, citrate, tartrate, fumarate, maleate and malate.

6. The compound according to claim 1, wherein B represents hydrogen, cyclohexyl,

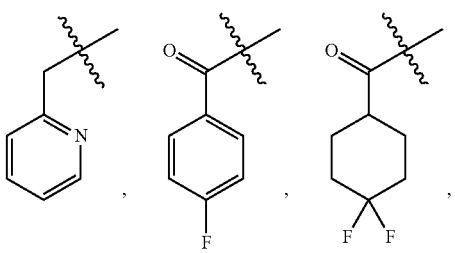

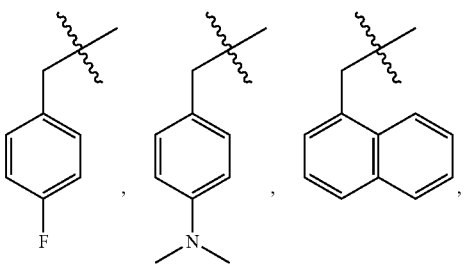

57
-continued
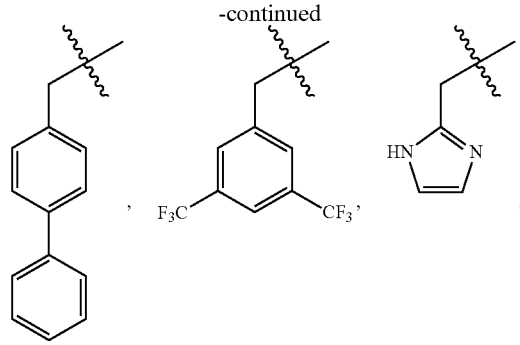
58
-continued
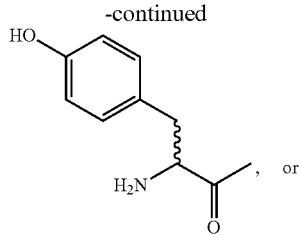
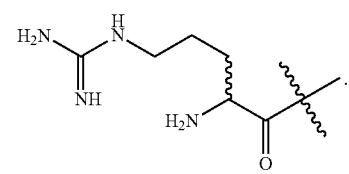
7. The compound according to claim 1, comprising one of the following structures:
(1)
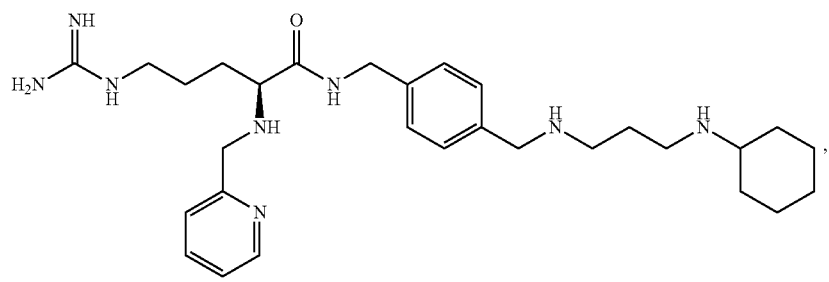
(2)
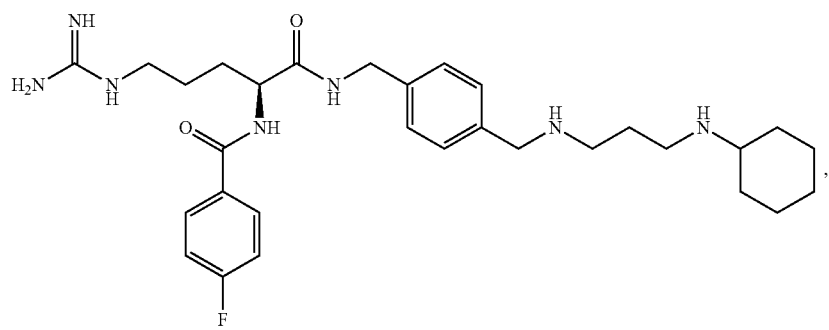
(5)
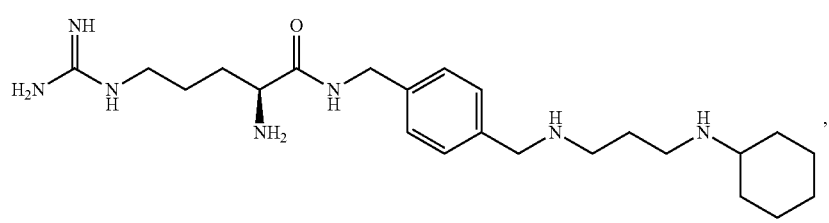

-continued
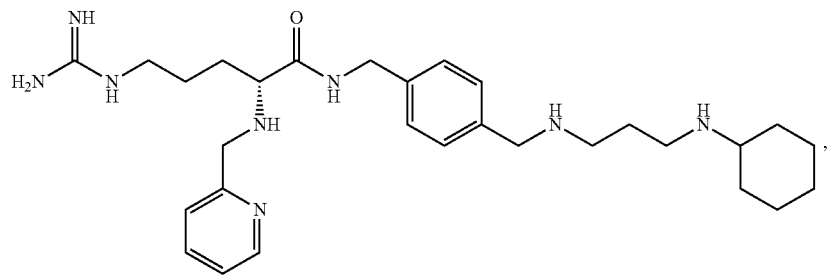
(6)
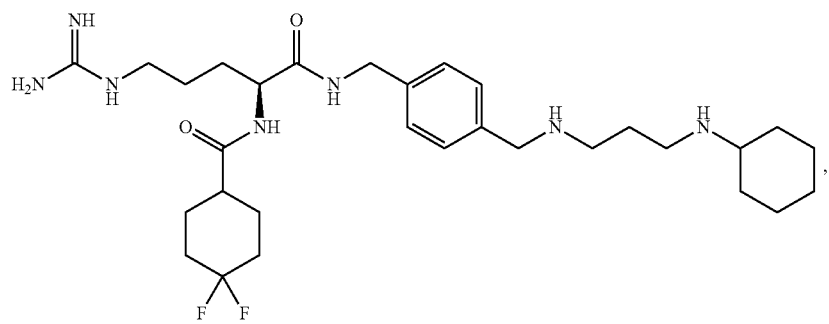
(7)
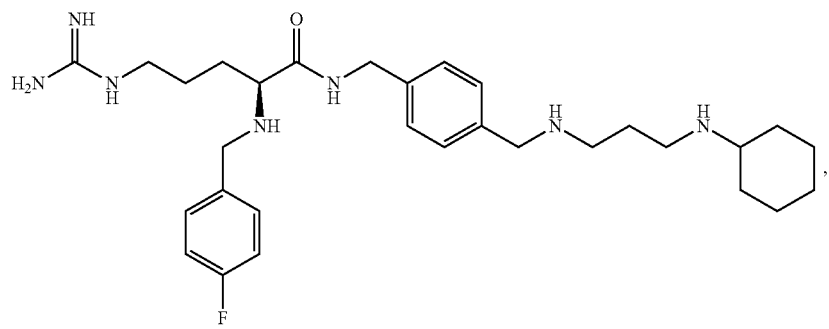
(8)
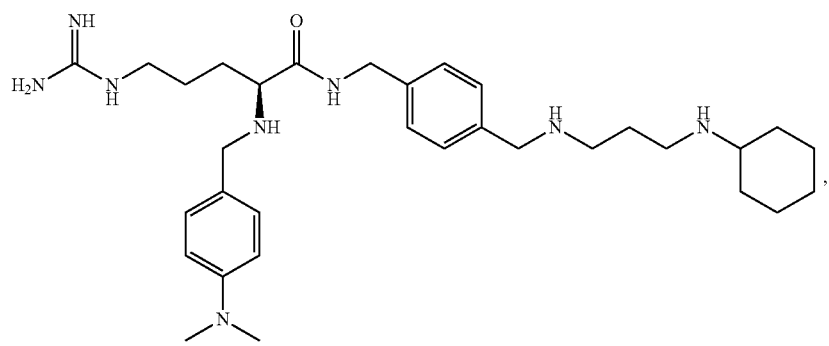
(9)
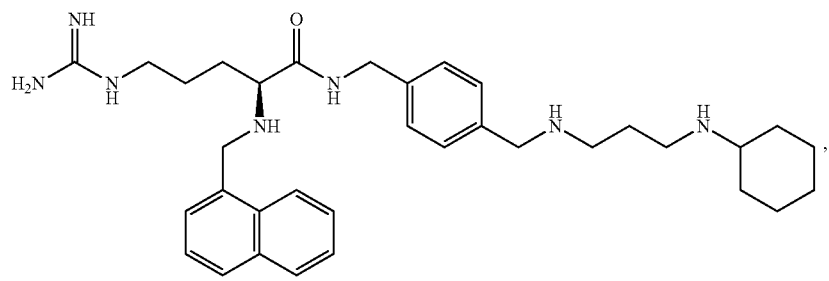
(10)

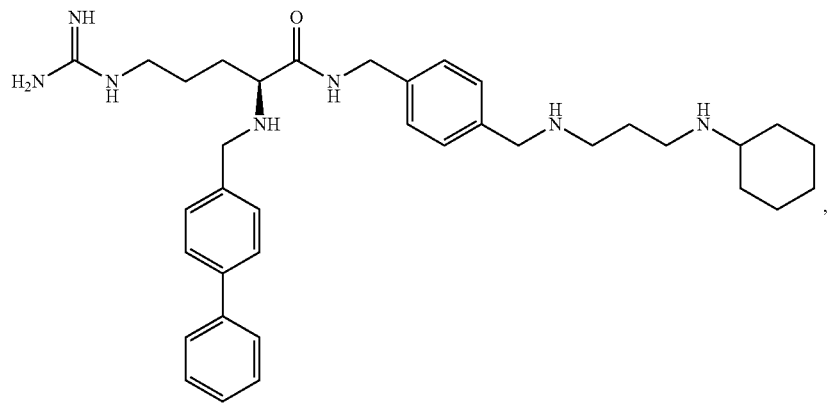
(11)
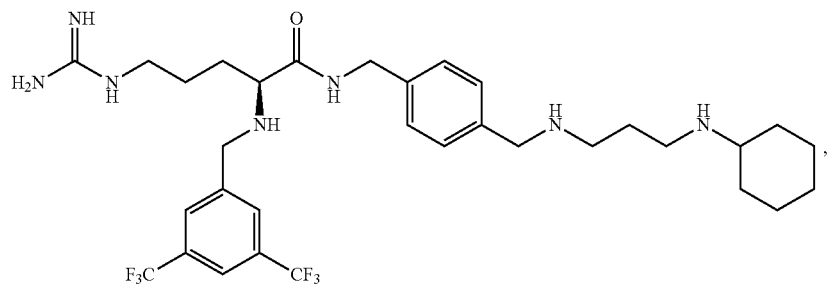
(12)
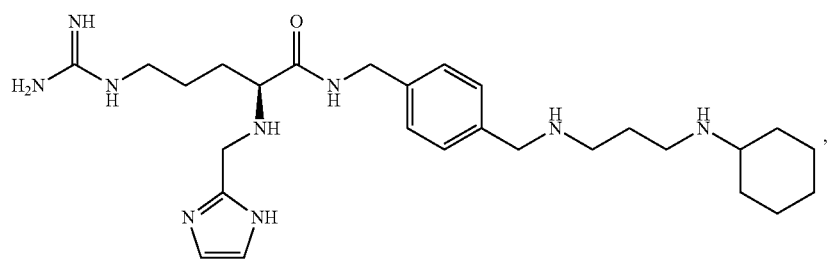
(13)
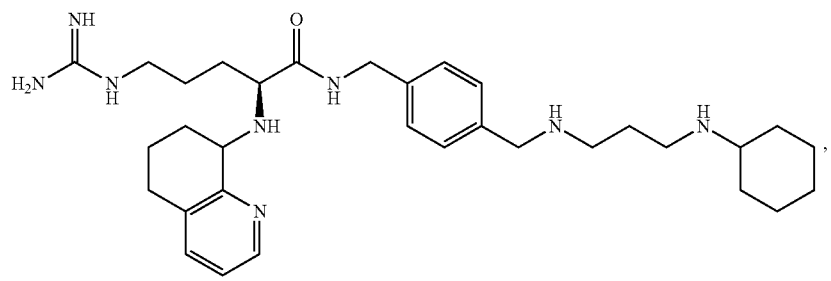
(14)
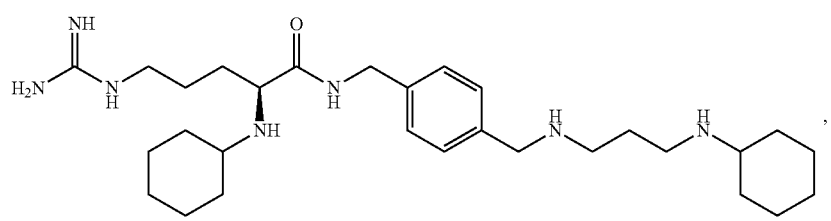
(15)

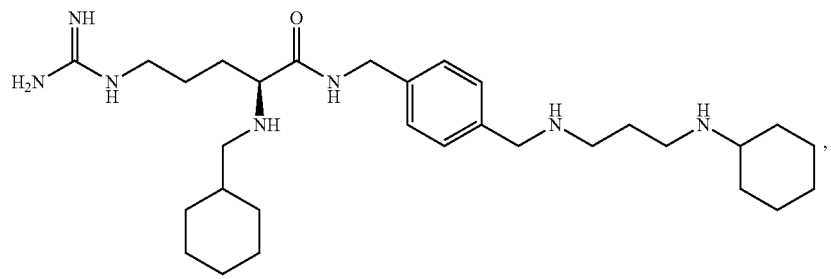
(16)
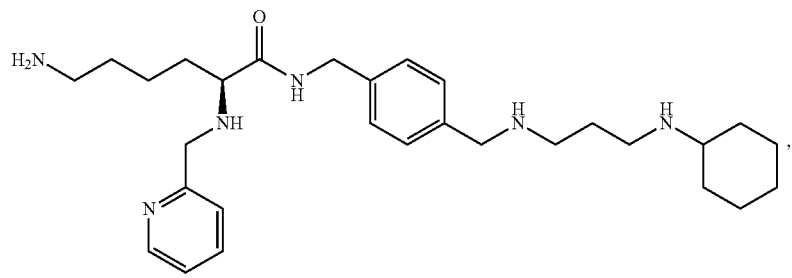
(17)
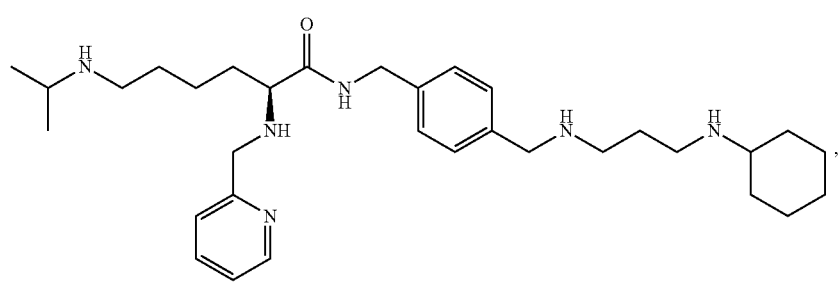
(18)
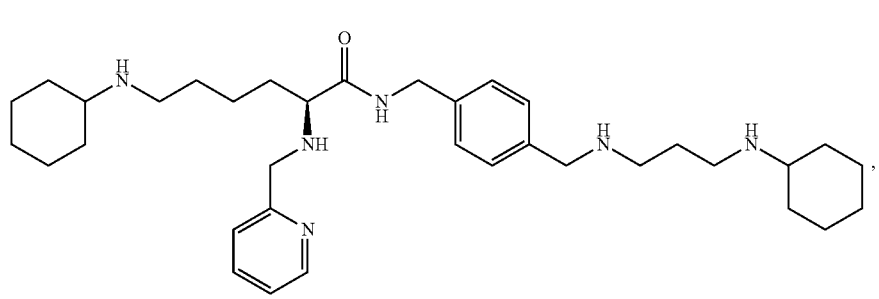
(19)
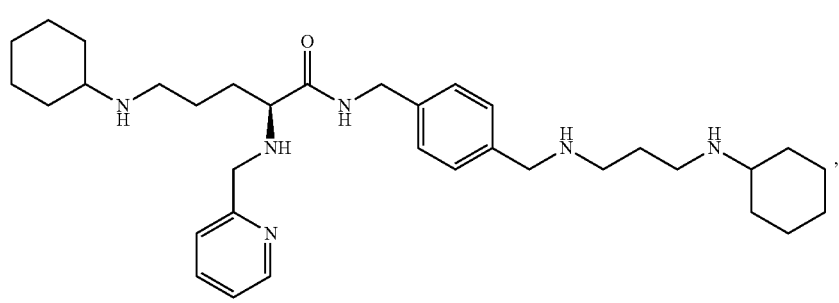
(20)

-continued
(21)
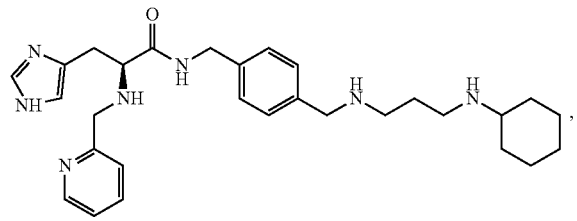
(22)
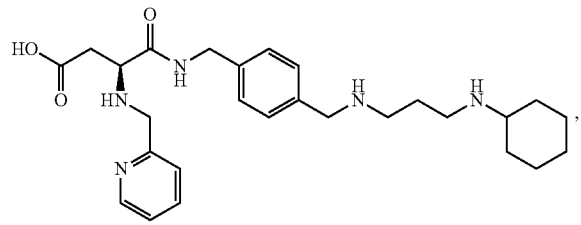
(23)
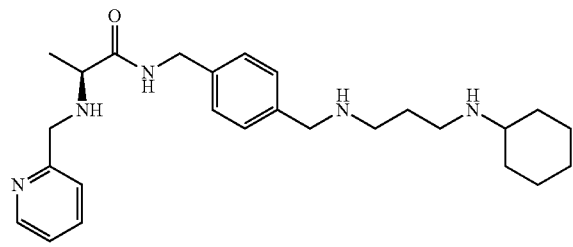
(24)
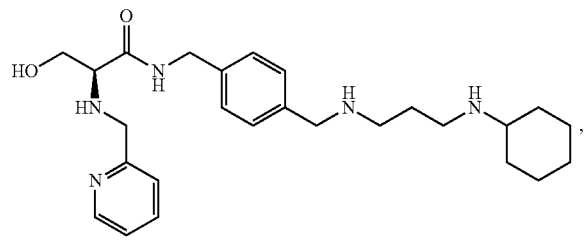
(25)
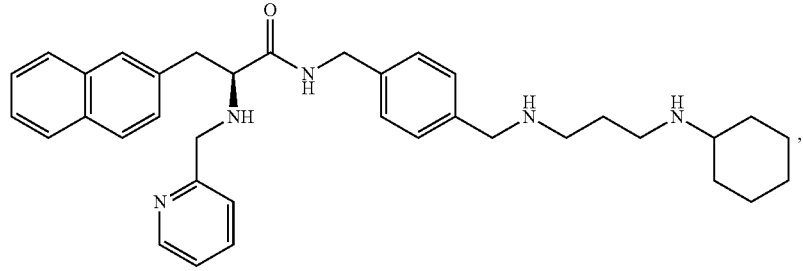
(26)
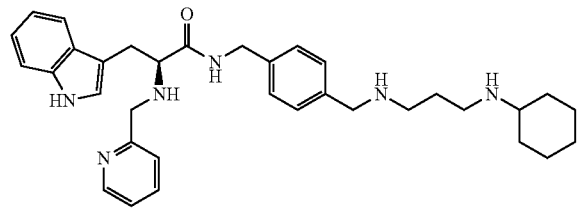
(27)
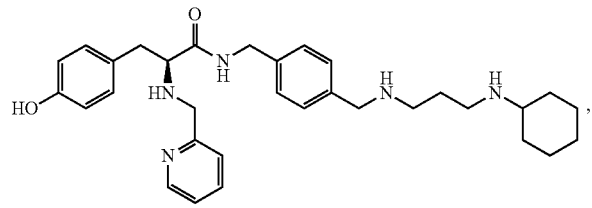
(28)
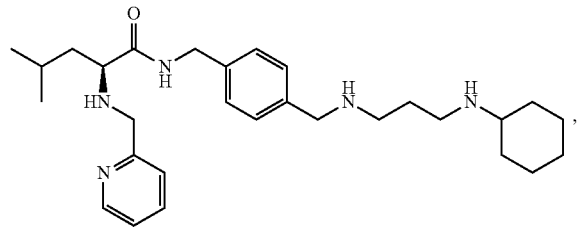
(29)
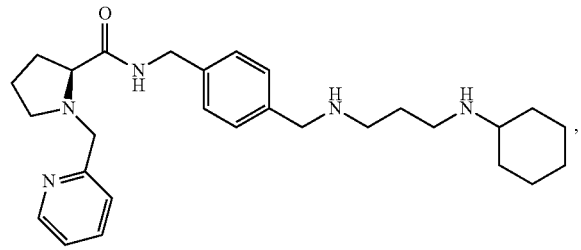
(30)
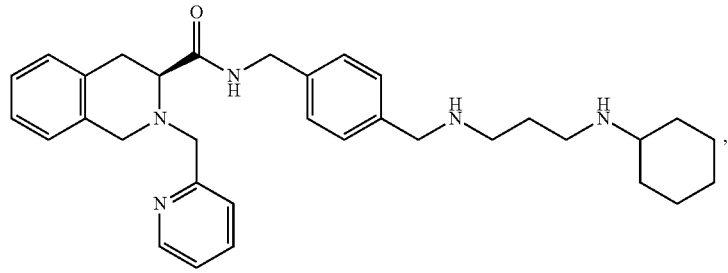

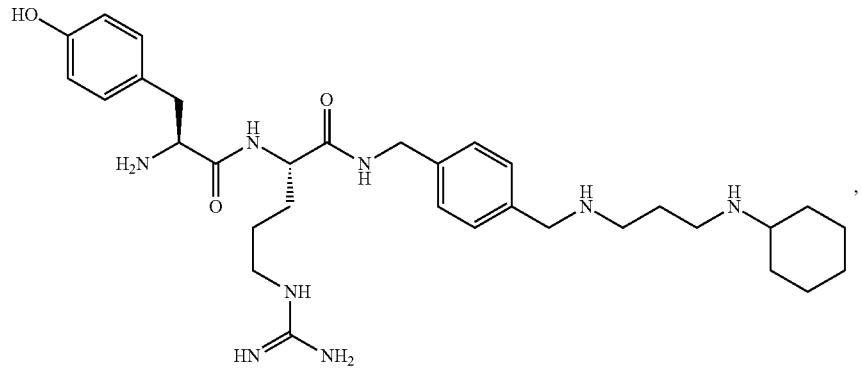

(31)

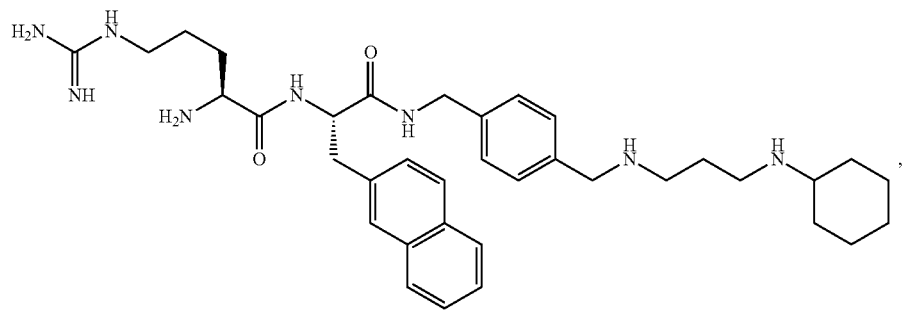

(32)

or a pharmaceutically acceptable salt or prodrug thereof.

8. A pharmaceutical composition, comprising a compound according to claim 1 as an active ingredient and a pharmaceutically acceptable auxiliary.

9. The pharmaceutical composition according to claim 8, further comprising one or more other anti-HIV agents,
wherein the other anti-HIV agent comprises at least one selected form a group comprising maraviroc, enfuvirtide, zidovudine, zalcitabine, stavudine, lamivudine, nevirapine, delavirdine, abacavir, efavirenz, tenofovir, emtricitabine, etravirine, and rilpivirine.

10. The pharmaceutical composition according to claim 9, further comprising
cisplatin, cyclophosphamide, cytarabine, 5-fluorouracil, gemcitabine, taxol, docetaxel, adriamycin, glivec, tarceva, sorafenib, dasatinib, lapatinib, sunitinib, erlotinib, gefitinib, cetuximab, or herceptin of trastuzumab.

11. The pharmaceutical composition according to claim 8, wherein the pharmaceutical composition is used for inhibiting interaction of a chemokine CXCL12 with a CXCR4 receptor or inhibiting the CXCR4 receptor.

12. The pharmaceutical composition according to claim 8, wherein inhibiting the CXCR4 receptor is realized by antagonizing the CXCR4 receptor,
wherein:
the pharmaceutical composition is used to block HIV from invading and infecting human target cells or to treat or prevent AIDS, or
the pharmaceutical composition is used to mobilize human bone marrow hematopoietic cells, mesenchymal stem cells or stem cells, or
the pharmaceutical composition is used to interfere with CXCL12/CXCR4-mediated cell migration and adhesion, or
the pharmaceutical composition is used to prevent or treat CXCR4-mediated tumor metastasis, invasion or growth, or
the pharmaceutical composition is used to block CXCL12/CXCR4-mediated autoimmune and inflammatory responses.

\* \* \* \* \*